United States Patent
Budde et al.

(10) Patent No.: US 11,889,853 B2
(45) Date of Patent: *Feb. 6, 2024

(54) SURFACE-REACTED CALCIUM CARBONATE IN FOOD

(71) Applicant: Omya International AG, Oftringen (CH)

(72) Inventors: Tanja Budde, Brittnau (CH); Anaïs Hecker, Lyss (CH); Lalit Sharma, Zofingen (CH); Laura De Miguel, Oftringen (CH)

(73) Assignee: Omya International AG, Oftringen (CH)

( * ) Notice: Subject to any disclaimer, the term of this patent is extended or adjusted under 35 U.S.C. 154(b) by 23 days.

This patent is subject to a terminal disclaimer.

(21) Appl. No.: 17/553,613

(22) Filed: Dec. 16, 2021

(65) Prior Publication Data

US 2022/0104525 A1    Apr. 7, 2022

Related U.S. Application Data

(62) Division of application No. 16/609,333, filed as application No. PCT/EP2018/062115 on May 9, 2018, now abandoned.

(60) Provisional application No. 62/522,191, filed on Jun. 20, 2017.

(30) Foreign Application Priority Data

May 11, 2017   (EP) .................................... 17170704

(51) Int. Cl.
| | | |
|---|---|---|
| *A23L 29/00* | (2016.01) | |
| *A23L 5/42* | (2016.01) | |
| *A23L 33/115* | (2016.01) | |
| *A23P 20/15* | (2016.01) | |
| *A23P 20/25* | (2016.01) | |
| *A61K 9/00* | (2006.01) | |
| *A61K 47/02* | (2006.01) | |
| *C09C 1/02* | (2006.01) | |

(52) U.S. Cl.
CPC .............. *A23L 29/015* (2016.08); *A23L 5/42* (2016.08); *A23L 33/115* (2016.08); *A23P 20/15* (2016.08); *A23P 20/25* (2016.08); *A61K 9/0056* (2013.01); *A61K 47/02* (2013.01); *C09C 1/021* (2013.01); *A23V 2002/00* (2013.01); *C01P 2004/61* (2013.01); *C01P 2006/12* (2013.01)

(58) Field of Classification Search
CPC ..... A61K 9/0056; A61K 47/02; A23L 29/015; A23L 5/42; A23L 33/115; A23P 20/15; A23P 20/25; A23V 2002/00; C01P 2004/61; C01P 2006/12; C09C 1/021
See application file for complete search history.

(56) References Cited

U.S. PATENT DOCUMENTS

| | | | |
|---|---|---|---|
| 4,681,766 A | 7/1987 | Huzinec et al. | |
| 10,351,710 B2 | 7/2019 | Gerard et al. | |
| 10,676,624 B2 | 6/2020 | Gane et al. | |
| 11,369,571 B2 * | 6/2022 | Diaz Quijano | A23L 27/77 |
| 11,400,050 B2 * | 8/2022 | Diaz Quijano | A23L 29/00 |
| 11,576,410 B2 * | 2/2023 | Budde | A23P 30/34 |
| 2004/0020410 A1 | 2/2004 | Gane et al. | |
| 2007/0142527 A1 | 6/2007 | Rosa et al. | |
| 2008/0031831 A1 | 2/2008 | Laali | |
| 2011/0305759 A1 | 12/2011 | Koehler | |
| 2012/0003360 A1 | 1/2012 | Barrett et al. | |
| 2014/0248340 A1 | 9/2014 | Schwarzentruber et al. | |
| 2017/0105911 A1 * | 4/2017 | Budde | A61K 8/19 |
| 2020/0187538 A1 | 6/2020 | Budde et al. | |

FOREIGN PATENT DOCUMENTS

| | | | |
|---|---|---|---|
| EP | 1712523 A1 | 10/2006 | |
| EP | 1712597 A1 | 10/2006 | |
| EP | 2264108 A1 | 12/2010 | |
| EP | 2264109 A1 | 12/2010 | |
| EP | 2371766 A1 | 10/2011 | |
| EP | 2447213 A1 | 5/2012 | |
| EP | 2524898 A1 | 11/2012 | |
| EP | 2770017 A1 | 8/2014 | |
| EP | 2997833 A1 * | 3/2016 | A23K 20/10 |
| EP | 2997833 A1 | 3/2016 | |
| JP | H03127939 | 5/1991 | |
| JP | H11292791 A | 10/1999 | |
| JP | 2008125482 | 6/2008 | |
| JP | 2010043036 | 2/2010 | |
| WO | WO-0039222 A1 | 7/2000 | |
| WO | 0247488 | 6/2002 | |
| WO | WO-2004083316 A1 | 9/2004 | |
| WO | WO-2005121257 A2 | 12/2005 | |

(Continued)

OTHER PUBLICATIONS

Gerard et al CN 106132384 A1, Eng. Trans, 2016. (Year: 2016).*
"U.S. Appl. No. 16/609,333, Advisory Action dated Aug. 5, 2021", 5 pgs.

(Continued)

*Primary Examiner* — Blessing M Fubara

(74) *Attorney, Agent, or Firm* — Schwegman Lundberg & Woessner, P.A.

(57) ABSTRACT

The present invention refers to an edible composition comprising water and/or at least one edible oil and a surface reacted calcium carbonate having a volume median particle size $d_{50}$ from 0.1 to 90 μm, an edible coating and/or filling comprising the surface-reacted calcium carbonate, a food product or pharmaceutical product or neutraceutical product at least partially coated and/or filled with the edible composition, a method for producing a food product or pharmaceutical product or neutraceutical product at least partially coated and/or filled with the edible composition.

16 Claims, 7 Drawing Sheets

(56) References Cited

FOREIGN PATENT DOCUMENTS

| WO | WO-2005122799 A1 | 12/2005 |
|----|------------------|---------|
| WO | WO-2009074492 A1 | 6/2009  |
| WO | WO-2013061061 A1 | 5/2013  |
| WO | WO-2013142473 A1 | 9/2013  |
| WO | 2015017606       | 2/2015  |
| WO | WO-2015150011 A1 | 10/2015 |
| WO | WO-2016046051 A1 | 3/2016  |
| WO | WO-2016110459 A1 | 7/2016  |

OTHER PUBLICATIONS

"U.S. Appl. No. 16/609,333, Final Office Action dated May 24, 2021", 21 pgs.

"U.S. Appl. No. 16/609,333, Non Final Office Action dated Dec. 16, 2020", 20 pgs.

"U.S. Appl. No. 16/609,333, Response filed Mar. 1, 2021 to Non Final Office Action dated Dec. 16, 2020", 10 pgs.

"U.S. Appl. No. 16/609,333, Response filed Jul. 20, 2021 to Final Office Action dated May 24, 2021", 10 pgs.

"U.S. Appl. No. 16/609,333, Response filed Sep. 23, 2020 to Restriction Requirement dated Aug. 20, 2020", 8 pgs.

"U.S. Appl. No. 16/609,333, Response filed Nov. 23, 2021 to Advisory Action dated Aug. 5, 2021", 11 pgs.

"U.S. Appl. No. 16/609,333, Restriction Requirement dated Aug. 20, 2020", 10 pgs.

Gane, Patrick A, et al., "Void Space Structure of Compressible Polymer Spheres and Consolidated Calcium Carbonate Paper-Coating Formulations", Industrial and Engineering Chemistry Research, 35(5), (1996), 1753-1764.

"U.S. Appl. No. 16/609,333, Non Final Office Action dated Dec. 21, 2021", 23 pgs.

U.S. Appl. No. 16/609,333, filed Oct. 29, 2019, Surface-Reacted Calcium Carbonate in Food.

\* cited by examiner

SURFACE-REACTED CALCIUM CARBONATE IN FOOD

CROSS-REFERENCE TO RELATED APPLICATIONS

This application is a continuation of U.S. patent application Ser. No. 16/609,333, filed Oct. 29, 2019, which is a U.S. National Stage Filing under 35 U.S.C. 371 from International Application No. PCT/EP20181062115, filed on May 9, 2018, and published as WO 2018/206709 on Nov. 15, 2018, which claims priority to Application Ser. No. 62/522,191, filed Jun. 20, 2017, which claims priority to European Application Serial No. 17170704.5, filed May 11, 2017, which applications are incorporated herein by reference in their entirety.

The present invention refers to an edible composition comprising water and/or at least one edible oil and a surface-reacted calcium carbonate having a volume median particle size $d_{50}$ from 0.1 to 90 µm, an edible coating and/or filling comprising the surface-reacted calcium carbonate, a food product or pharmaceutical product or neutraceutical product at least partially coated and/or filled with the edible composition, a method for producing a food product or pharmaceutical product or neutraceutical product at least partially coated and/or filled with the edible composition and the uses of the surface-reacted calcium carbonate as whitening agent or pacifier and/or sweetness reduction agent and/or calorie reduction agent in an edible coating and/or filling of a food product or pharmaceutical product or neutraceutical product, as a replacement agent for titanium dioxide in an edible coating and/or filling of a food product or pharmaceutical product or neutraceutical product as well as for reducing the dry time of an edible composition being at least partially applied on the surface of and/or filled into a food product or pharmaceutical product or neutraceutical product.

A variety of food product such as cakes, cookies, candies, cereals, cereal bars, chips, chewing gum, ice cream wafer and the like, but also pharmaceutical or neutraceutical products such as tablets, mini-tables, pellets, capsules, granules and the like, are coated or filled with an edible composition. Often such compositions are applied to modify the appearance of the food product, i.e. for decoration purposes, to protect the food product, i.e. against or to impart specific properties such as sweetness to the product.

Several edible compositions are known in the prior art. Exemplarily, reference is made to WO 2013/061061 A1 refers to a paint for use in the decoration of food, for example, for use in cake decoration. Specifically, it is referred to metallic aqueous paints, including edible paints, comprising a pearlescent pigment, an acidity regulator, an emulsifier and a starch and optionally comprising a preservative and/or a coloured pigment. The application further relates to processes for the manufacture of said paints and processes for decorating a food product, such as a cake, using said paint. The application also refers to food products decorated with said paint JP 11-292791 A refers to a preparation or food which is obtained by including one or more kinds of (A) calcium salts of an inorganic acid, (B) magnesium salts of the inorganic acid and (C) titanium oxide having the particle surface subjected to a coating treatment with other components as a white pigment WO2016/046051 A1 relates to the use of a surface-reacted calcium carbonate as anti-caking agent, wherein the surface-reacted calcium carbonate is a reaction product of natural ground or precipitated calcium carbonate with carbon dioxide and at least one acid in an aqueous medium, wherein the carbon dioxide is formed in situ by the acid treatment and/or is supplied from an external source, and to a composition comprising said anti-caking agent, as well as to a method for the production of such a composition.

It is to be noted that the coatings of the prior art typically contain titanium dioxide due to its high brightness and covering power. However, high amounts of sugar are necessary to mask the flavor of the titanium dioxide such that these coatings and fillings are very sweet and high in calories. Furthermore, natural ground calcium carbonate (NGCC) and/or precipitated calcium carbonate (PCC) are known as white pigment in food applications. However, high amounts of natural ground calcium carbonate (NGCC) and/or precipitated calcium carbonate (PCC), e.g. in the range of 30 to 50 wt.-%, are to be used in order to achieve a sufficient covering power.

Thus, the provision of an edible composition being free of titanium dioxide remains of interest to the skilled man. Furthermore, it is desired to provide an edible composition providing a similar or the same brightness and/or covering power as titanium dioxide. In addition thereto, it is desired to reduce the amount of sugar and calories of such edible composition, preferably at a similar or the same brightness and/or covering power as titanium dioxide. Furthermore, it is desirable to provide an edible composition providing a similar or the same brightness and/or covering power as titanium dioxide but avoiding the use of excessive amounts of the pigment. Accordingly, it is an object of the present invention to provide an edible composition, preferably being free of titanium dioxide. Another object of the present invention is to provide an edible composition having high brightness and/or covering power, especially a similar or the same brightness and/or covering power as titanium dioxide. A further object of the present invention is to provide an edible composition in which the amount of sugar and calories is reduced, preferably at a similar or the same brightness and/or covering power as titanium dioxide. A further object of the present invention is to provide an edible composition providing a similar or the same brightness and/or covering power as titanium dioxide but avoiding the use of excessive amounts of pigments.

The foregoing objects and other objects are solved by the subject-matter as defined herein in the independent claims.

According to one aspect of the present invention, an edible: composition comprising water and/or at least one edible oil and a surface-reacted calcium carbonate having a volume median particle size $d_{50}$ from 0.1 to 90 µm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source is provided.

According to another aspect of the present invention, an edible coating and/or filling comprising a surface-reacted calcium carbonate having a volume median particle size $d_{50}$ from 0.1 to 90 µm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source is provided.

According to a further aspect of the present invention, a food product or pharmaceutical product or neutraceutical product at least partially coated and/or filled with the edible composition, as defined herein, is provided.

According to an even further aspect of the present invention, a method for producing a food product or pharmaceutical product or neutraceutical product at least partially coated and/or filled with the edible composition, as defined herein, is provided. The method comprising the steps of
a) mixing water and/or at least one edible oil with a surface-reacted calcium carbonate having a volume median particle size $d_{50}$ from 0.1 to 90 µm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, for obtaining an edible composition, and
b) applying the edible composition obtained in step a), one or more times, at least partially on the surface of a food product or pharmaceutical product or neutraceutical product, or filling the edible composition obtained in step a) into a food product or pharmaceutical product or neutraceutical product.

According to another aspect of the present invention, the use of a surface-reacted calcium carbonate having a volume median particle size $d_{50}$ from 0.1 to 90 µm as whitening agent or opacifier and/or sweetness reduction agent and/or calorie reduction agent in an edible coating and/or filling of a food product or pharmaceutical product or neutraceutical product is provided, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

According to a further aspect of the present invention, the use of a surface-reacted calcium carbonate having a volume median particle size $d_{50}$ from 0.1 to 90 µm as a replacement agent for titanium dioxide in an edible coating and/or filling of a food product or pharmaceutical product or neutraceutical product is provided, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

According to an even further aspect of the present invention, the use of a surface-reacted calcium carbonate having a volume median particle size $d_{50}$ from 0.1 to 90 µm for reducing the dry time of an edible composition being at least partially applied on the surface of and/or filled into a food product or pharmaceutical product or neutraceutical product is provided, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

Advantageous embodiments of the inventive use are defined in the corresponding sub-claims.

According to one embodiment, the surface-reacted calcium carbonate has a volume median particle size $d_{50}$ from 0.1 to 75 µm, preferably from 0.5 to 50 µm, more preferably from 1 to 40 µm, even more preferably from 1.2 to 30 µm, and most preferably from 1.5 to 15 µm.

According to another embodiment, the surface-reacted calcium carbonate has a specific surface area of from 15 $m^2/g$ to 200 $m^2/g$, preferably from 20 $m^2/g$ to 180 $m^2/g$, more preferably from 25 $m^2/g$ to 160 $m^2/g$, even more preferably from 27 $m^2/g$ to 150 $m^2/g$, and most preferably from 30 $m^2/g$ to 140 $m^2/g$, measured using nitrogen and the BET method.

According to yet another embodiment, (i) the natural ground calcium carbonate is selected from the group consisting of marble, chalk, limestone, and mixtures thereof, or (ii) the precipitated calcium carbonate is selected from the group consisting of precipitated calcium carbonates having an aragonitic, vateritic or calcitic crystal form, and mixtures thereof.

According to one embodiment, the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof, preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $K^+$, $Mg^{2+}$, and/or $Ca^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

According to another embodiment, the surface-reacted calcium carbonate is present in an amount from 1.0 to 50.0 wt.-%, based on the total weight of the edible composition, preferably from 1.5 to 25.0 wt.-%, more preferably from 2.0 to 15.0 wt.-% and most preferably from 2.5 to 12.0 wt.-%.

According to yet another embodiment, the at least one edible oil is selected from the group comprising palm oil, sunflower oil, soybean oil, coconut oil, peanut oil, olive oil and mixtures thereof.

According to one embodiment, the edible composition further comprises one or more additives selected from the group consisting of icing sugar, starches, such as wheat starch, rice starch, tapioca starch, corn starch, potato starch, pre-gelatinized acetylated distarch adipate and mixtures thereof; binding agents, such as gum arabic, locastbean gum and mixtures thereof; waxes, such as carnauba wax, montan wax and mixtures thereof; preservatives, such as propionic acid, sorbic acid, benzoic acid and salts thereof; antioxidants, such as butylhydroxyanisol (BHA), ascorbic acid, tocopherol, propyl gal late, octyl gallate and mixtures thereof; stabilizers or texture modifier, such as agar agar, gelatin and mixtures thereof; proteins; emulsifier, such as emulsifier comprising sucrose ester or lecithin or sorbitane monostearates and mixtures thereof, flavours, artificial sweetener, sugar such as fructose, glucose, sucrose, glucose-fructose mixtures, maltose and mixtures thereof, and polyols such as mannitol, sorbitol, xylitol, isomalt, glycerol, maltitol, erythritol, lactitol and mixtures thereof, defoaming agents, surfactants, colorants, plasticizers and film-forming agents.

According to another embodiment, the edible composition further comprises at least one natural ground calcium carbonate (NGCC) and/or at least one precipitated calcium carbonate (PCC), preferably the at least one natural ground calcium carbonate (NGCC) and/or at least one precipitated calcium carbonate (PCC) has/have a weight median particle size $d_{50}$ from 0.05 to 100 µm, more preferably from 0.1 to 75 µm, even more preferably from 0.25 to 50 µm, and most preferably from 0.5 to 40 µm.

According to yet another embodiment, the edible composition is a food coating, sugar coating, sugar-free coating, nutra coating, food decoration, food filling, pharmaceutical coating and the like.

According to one embodiment, the food product is selected from cakes, cookies, candies, cereals, cereal bars, chips, chewing gum, ice cream wafer and the like, or the pharmaceutical product or neutraceutical product is selected from tablets, mini-tables, pellets, capsules, granules and the like.

According to one embodiment of the present method, applying the edible composition obtained in step a) at least partially on the surface of a food product or pharmaceutical product or neutraceutical product in step b) is carried out by brushing or pouring, pan coating, curtain or dip coating, fluidized bed coating, hot melt coating and/or compression coating or the filling of the edible composition obtained in step a) into a food product or pharmaceutical product or neutraceutical product in step b) is carried out by injecting the edible composition into the food product or pharmaceutical product or neutraceutical product.

It should be understood that for the purposes of the present invention, the following terms have the following meanings:

"Edible" composition in the meaning of the present invention refers to a composition that is taken up orally.

"Natural ground calcium carbonate" (GCC) in the meaning of the present invention is a calcium carbonate Obtained from natural sources, such as limestone, marble, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. PCCs are described, for example, in EP 2 447 213 A1, EP 2 524 898 A1, EP 2 371 766 A1, EP 1 712 597 A1, EP 1 712 523 A1, or WO 2013/142473 A1.

The term "surface-reacted" in the meaning of the present application shall be used to indicate that a material has been subjected to a process comprising partial dissolution of said material upon acidic treatment (e.g., by use of water-soluble free acids and/or acidic salts) in aqueous environment followed by a crystallization process which may occur in the absence or presence of further crystallization additives. The term "acid" as used herein refers to an acid in the meaning of the definition by Brønsted and Lowry (e.g., $H_2SO_4$, $HSO_4^-$), wherein the term "free acid" refers only to those acids being in the fully protonated form (e.g., $H_2SO_4$).

The "particle size" of particulate materials other than surface-reacted calcium carbonate herein is described by its distribution of particle sizes $d_x$. Therein, the value $d_x$ represents the diameter relative to which x % by weight of the particles have diameters less than $d_x$. This means that, for example, the $d_{20}$ value is the particle size at which 20 wt.-% of all particles are smaller than that particle size. The $d_{50}$ value is thus the weight median particle size, i.e. 50 wt.-% of all particles are smaller than this particle size. For the purpose of the present invention, the particle size is specified as weight median particle size $d_{50}$(wt.) unless indicated otherwise. Particle sizes were determined by using a Sedigraph™ 5100 instrument or Sedigraph™ 5120 instrument of Micromeritics Instrument Corporation. The method and the instrument are known to the skilled person and are commonly used to determine the particle size of fillers and pigments. The measurements were carried out in an aqueous solution of 0.1 wt.-% $Na_4P_2O_7$.

The "particle size" of surface-reacted calcium carbonate herein is described as volume-based particle size distribution. Volume median particle size the was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The term "particulate" in the meaning of the present application refers to materials composed of a plurality of particles. Said plurality of particles may be defined, for example, by its particle size distribution. The expression "particulate material" may comprise granules, powders, grains, tablets, or crumbles.

The "specific surface area" (expressed in $m^2/g$) of a material as used throughout the present document can be determined by the Brunauer Emmett Teller (BET) method with nitrogen as adsorbing gas and by use of a ASAP 2460 instrument from Micromeritics. The method is well known to the skilled person and defined in ISO 9277:2010. Samples are conditioned at 100° C. under vacuum for a period of 30 min prior to measurement. The total surface area (in $m^2$) of said material can be obtained by multiplication of the specific surface area (in $m^2/g$) and the mass (in g) of the material.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

Unless specified otherwise, the term "drying" refers to a process according to which at least a portion of water is removed from a material to be dried such that a constant weight of the obtained "dried" material at 120° C. is reached. Moreover, a "dried" or "dry" material may be defined by its total moisture content which, unless specified otherwise, is less than or equal to 1.0 wt.-%, preferably less than or equal to 0.5 wt.-%, more preferably less than or equal to 0.2 wt.-%, and most preferably between 0.03 and 0.07 wt.-%, based on the total weight of the dried material.

For the purpose of the present application, "water-insoluble" materials are defined as those which, when mixed with 100 ml of deionised water and filtered at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of solid material following evaporation at 95 to 100° C. of 100 g of said liquid filtrate. In order to assess whether a material is an insoluble or soluble material in the meaning of the present invention, the sample size is greater than 0.1 g, preferably 0.5 g or more.

A "suspension" or "slurry" in the meaning of the present invention comprises undissolved solids and water, and optionally further additives, and usually contains large amounts of solids and, thus, is more viscous and can be of higher density than the liquid from which it is formed.

Where an indefinite or definite article is used when referring, to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by t terms "obtained" or "defined" as a preferred embodiment.

Whenever the terms "including" or "having" are used, these terms are meant to be equivalent to "comprising" as defined hereinabove.

In the following preferred embodiments of the inventive edible composition will be set out in more detail. It is to be understood that these embodiments and details also apply to the inventive products, methods and uses.

Edible Composition

The edible composition of the present invention comprises water and/or at least one edible oil and a surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

Accordingly, it is one requirement of the present invention that the edible composition comprises a surface-reacted calcium carbonate having a volume median particle size $d_{50}$ from 0.1 to 90 μm.

In this regard, the inventors surprisingly found out that such a surface-reacted calcium carbonate can be used in an edible composition as a replacement agent for titanium dioxide and thus compositions being free of titanium dioxide can be provided. Furthermore, the inventors found out that the surface-reacted calcium carbonate has a high brightness and/or covering power in an edible composition, which is similar or the same as for titanium dioxide. In addition thereto, the inventors surprisingly found that the amount of sugar and calories is reduced, preferably at a similar or the same brightness and/or covering power as titanium dioxide, when the surface-reacted calcium carbonate is used in an edible composition. Furthermore, the inventors surprisingly found out that a similar or the same brightness and/or covering power as titanium dioxide, when the surface-reacted calcium carbonate is used in an edible composition, but avoids the use of excessive amounts of natural ground calcium carbonate (NGCC) and/or precipitated calcium carbonate (PCC).

An $H_3O^+$ ion donor in the context of the present invention is a Brønsted acid and/or an acid salt, i.e. a salt containing an acidic hydrogen.

In a preferred embodiment of the invention the surface-reacted calcium carbonate is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural ground calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man, in case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production: Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural ground calcium carbonate or precipitated calcium carbonate is in form of particles having a weight median particle size $d_{50}$ of 0.05 to 10.0 μm, preferably 0.2 to 5.0 μm, more preferably 0.4 to 3.0 μm, most preferably 0.5 to 1.2 μm, especially 0.6 μm.

According to a further embodiment of the present invention, the natural ground calcium carbonate or precipitated calcium carbonate is in form of particles having a weight top cut particle size $d_{98}$ of 0.15 to 30 μm, preferably 0.6 to 15 μm, more preferably 1.2 to 10 μm, most preferably 1.5 to 4 μm, especially 1.6 μm.

The natural ground calcium carbonate and/or precipitated calcium carbonate may be used dry or suspended in water. Preferably, a corresponding slurry has a content of natural ground calcium carbonate or precipitated calcium carbonate within the range of 1 wt.-% to 90 wt-%, more preferably 3 wt.-% to 60 wt.-%, even more preferably 5 wt.-% to 40 wt.-%, and most preferably 10 wt.-% to 25 wt-% based on the weight of the slurry.

The one or more $H_3O^+$ ion donor used for the preparation of surface-reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic add, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural ground calcium carbonate or precipitated calcium carbonate is treated with carbon dioxide. If a strong acid such as sulphuric acid or hydrochloric acid is used for the $H_3O^+$ ion donor treatment of the natural ground calcium carbonate or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1, US 2004/0020410 A1 and unpublished European patent application no. 16181094.0, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural ground calcium carbonate or precipitated calcium carbonate, the natural ground calcium carbonate or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural ground calcium carbonate or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural ground calcium carbonate or precipitated calcium carbonate in the form of granules or a powder.

The surface-reacted calcium carbonate may have different particle shapes, such as e.g. the shape of roses, golf balls and/or brains.

According to one embodiment the surface-reacted calcium carbonate has a specific surface area of from 15 m$^2$/g to 200 m$^2$/g, preferably from 20 m$^2$/g to 180 m$^2$/g, more preferably from 25 m$^2$/g to 160 m$^2$/g, even more preferably from 27 m$^2$/g to 150 m$^2$/g, most preferably from 30 m$^2$/g to 140 m$^2$/g, measured using nitrogen and the BET method. The BET specific surface area in the meaning of the present invention is defined as the surface area of the particles divided by the mass of the particles. As used therein the specific surface area is measured by adsorption using the BET isotherm (ISO 9277:2010) and is specified in m$^2$/g.

It is a requirement of the present invention that the surface-reacted calcium carbonate has a volume median particle size $d_{50}$ from 0.1 to 90 µm. According to one embodiment the surface-reacted calcium carbonate has a volume median particle size $d_{50}$ from 0.1 to 75 µm, preferably from 0.5 to 50 µm, more preferably from 1 to 40 µm, even more preferably from 1.2 to 30 µm, and most preferably from 1.5 to 15 µm.

It may furthermore be preferred that the surface-reacted calcium carbonate particles have a volume top cut particle size $d_{98}$ of from 2 to 150 µm, preferably from 4 to 100 µm, more preferably 6 to 80 µm, even more preferably from 8 to 60 µm, and most preferably from 10 to 30 µm.

The value $d_x$ represents the diameter relative to which x % of the particles have diameters less than $d_x$. This means that the $d_{98}$ value is the particle size at which 98% of all particles are smaller. The $d_{98}$ value is also designated as "top cut". The $d_x$ values may be given in volume or weight percent. The $d_{50}$(wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005. The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 5 cm³ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p. 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine interparticle packing of the particles themselves. If they also have intraparticle pores, then this region appears bi-modal, and by taking the specific pore volume intruded by mercury into pores finer than the modal turning point, i.e. finer than the bimodal point of inflection, the specific intraparticle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the surface-reacted calcium carbonate has an intra-particle intruded specific pore volume in the range from 0.1 to 2.3 cm³/g, more preferably from 0.2 to 2.0 cm³/g, especially preferably from 0.4 to 1.8 cm³/g and most preferably from 0.6 to 1.6 cm³/g, calculated from mercury porosimetry measurement.

The intra-particle pore size of the surface-reacted calcium carbonate preferably is in a range of from 0.004 to 1.6 μm, more preferably in a range of between 0.005 to 1.3 μm, especially preferably from 0.006 to 1.15 μm and most preferably of 0.007 to 1.0 μm, e.g. 0.004 to 0.6 μm determined by mercury porosimetry measurement. According to an exemplary embodiment, the surface-reacted calcium carbonate has a volume median particle size $d_{50}$ from 1.5 to 15 μm, preferably from 1.5 to 2; a specific surface-area of from 30 to 140 m²/g, preferably from 40 to 60 m²/g, measured using nitrogen and the BET method; and an intra-particle intruded specific pore volume from 0.2 to 2.0 cm³/g, preferably from 0.2 to 0.4 cm³/g, calculated from mercury porosimetry measurement.

Due to the intra and interpore structure of the surface-reacted calcium carbonate, it can be a superior agent to deliver previously adsorbed and/or absorbed materials over time relative to common materials having similar specific surface areas. Thus, generally, any agent fitting into the intra- and/or inter particle pores of the surface-reacted calcium carbonate is suitable to be transported by the surface-reacted, calcium carbonate according to the invention. For example, active agents such as those selected from the group comprising pharmaceutically active agents, biologically active agents, disinfecting agents, preservatives, flavouring agents, surfactants, oils, fragrances, essential oils, and mixtures thereof can be used. According to one embodiment, at least one active agent is associated with the surface-reacted calcium carbonate.

According to one embodiment of the present invention, the surface-reacted calcium carbonate comprises an water-insoluble, at least partially crystalline calcium salt of an anion of the at least one acid, which is formed on the surface of the natural ground calcium carbonate or precipitated calcium carbonate. According to one embodiment, the water-insoluble, at least partially crystalline salt of an anion of the at least one acid covers the surface of the natural ground calcium carbonate or precipitated calcium carbonate at least partially, preferably completely. Depending on the employed at least one acid, the anion may be sulphate, sulphite, phosphate, citrate, oxalate, acetate, formiate and/or chloride.

For example, the use of phosphoric acid, $H_2PO_4^-$ or $HPO_4^{2-}$ as the $H_3O^+$ ion donor may lead to the formation of hydroxylapatite. Therefore, in a preferred embodiment, the at least one water-insoluble calcium salt is hydroxylapatite.

According to one embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Preferably, the surface-reacted calcium carbonate may provide a ratio of hydroxyl apatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

According to one embodiment the surface-reacted calcium carbonate comprises:
(i) a specific surface area of from 15 to 200 reg measured using nitrogen and the BET method according to 9277: 2010, and
(ii) an intra-particle intruded specific pore volume in the range of from 0.1 to 2.3 cm$^3$/g calculated from mercury porosimetry measurement.

It is appreciated that the edible composition is typically provided in form of a liquid composition which can be easily filled into and/or coated onto a food product or pharmaceutical product or neutraceutical product.

Thus, the edible composition comprises water and/or at least one edible oil.

It is appreciated that the water can be any water suitable for human or animal consumption, e.g. drinking water, tap water, mineral water, spring water and the like.

Additionally or alternatively, the edible composition comprises at least one edible oil.

The term "at least one" oil in the meaning of the present invention means that the oil comprises, preferably consists of, one or more oil(s).

In one embodiment of the present invention, the at least one oil comprises, preferably consists of, one oil. Alternatively, the at least one oil comprises, preferably consists of, two or more oil(s). For example, the at least one oil comprises, preferably consists of, two or three oils. Preferably, the at least one oil comprises, preferably consists of, one oil.

It is appreciated that the at least one oil can be any oil which is suitable for human or animal consumption. For example, the at least one edible oil is selected from the group comprising palm oil, sunflower oil, soybean oil, coconut oil, peanut oil, olive oil and mixtures thereof.

It is preferred that the edible composition comprises water. This is advantageous as the edible composition is preferably coated onto and/or filled into a product and then dried to obtain the corresponding edible coating and/or filling.

It is appreciated that the amount of the surface-reacted calcium carbonate in the edible composition may vary in a wide range and may be dependent on the composition to be prepared and/or the manufacturer's needs and/or legal requirements.

According to one embodiment of the present invention, the surface-reacted calcium carbonate is present in the edible composition in an amount from 1.0 to 50.0 wt.-%, based on the total weight of the edible composition, preferably from 1.5 to 25.0 wt.-%, more preferably from 2.0 to 15.0 wt.-% and most preferably from 2.5 to 12.0 wt.-%.

In this regard, the inventors surprisingly found out that the surface-reacted calcium carbonate provides a similar or the same brightness and/or covering power as titanium dioxide, but avoids the use of excessive amounts of natural ground calcium carbonate (NGCC) and/or precipitated calcium carbonate (PCC), i.e. amounts of from 30 to 50 wt.-%.

The edible composition may also comprise one or more additive(s). It is appreciated that the one or more additive(s) can be any additives) suitable for human or animal consumption.

According to one embodiment of the present invention, the edible composition further comprises one or more additives selected from the group consisting of icing sugar; starches; binding agents; waxes; preservatives; antioxidants; stabilizers or texture modifier; proteins; emulsifier; flavours; artificial sweetener; sugar, polyols, defoaming agents, surfactants, colorants, plasticizers and film-forming agents.

For example, the starch can be selected from the group comprising wheat starch, rice starch, tapioca starch, corn starch, potato starch, pre-gelatinized acetylated distarch adipate and mixtures thereof.

The binding agent may be selected from a natural and/or synthetic binding agent known as being suitable in edible compositions. For example, the binding agent is selected from gum arabic, locastbean gum and mixtures thereof.

The wax may be selected from a natural and/or synthetic wax such as carnauba wax, montan wax and mixtures thereof.

According to one embodiment, the preservative is preferably selected from propionic acid, sorbic acid, benzoic acid and salts thereof.

The antioxidant can be selected from the group comprising butylhydroxyanisol (BHA), ascorbic acid, tocopherol, propyl gallate, octyl gallate and mixtures thereof.

The stabilizer or texture modifier is preferably selected from agar agar, gelatin and mixtures thereof.

Additionally or alternatively, the edible composition comprises an emulsifier. Examples of suitable emulsifier are emulsifier comprising sucrose ester or lecithin or sorbitane monostearates and mixtures thereof. Such emulsifier are well known in the art and are available from a great variety of sources and do not be described in more detail in the present application.

Additionally or alternatively, the edible composition comprises a polyol. Examples of suitable polyols are mannitol, sorbitol, xylitol, isomalt, glycerol, maltitol, erythritol, lactitol and mixtures thereof.

Additionally or alternatively, the edible composition comprises one or more additive(s) selected from proteins; flavours; colorants; and artificial sweetener such as aspartame, cyclamate, saccharine, acesulfame potassium, stevia, mogrosides or sucralose.

Additionally or alternatively, the edible composition comprises one or more sugar(s). Examples of suitable sugar(s) include fructose, glucose, sucrose, glucose-fructose mixtures, maltose and mixtures thereof. The one or more sugar(s) can be in the form of rock sugar, brown sugar, icing sugar, syrup or invert sugar, preferably icing sugar.

Additionally or alternatively, the edible composition comprises a defoaming agent. Examples of suitable defoaming agents include silicones, silanes such as polydimethylsiloxane (PDMS) hydrophobic silica, silicones such as dimethicones or simethicones; and mixtures thereof.

Additionally or alternatively, the edible composition comprises a surfactant. Examples of suitable surfactants include polyether-modified siloxane surfactants, sodium lauryl sulphate (SLS), polysorbates, poloxamers and mixtures thereof.

Additionally or alternatively, the edible composition comprises a plasticizer. Examples of suitable plasticizers include triethyl citrate, diethyl phthalate, diacetin, triacetin, dibutyl phthalate, dibutyl tartrate, tributyl acetate, castor oil, cetyl alcohol, cetylstearyl alcohol, fatty acids, glycerides and triglycerides and polyoxyethylene glycols, preferably polyoxyethylene glycols having molecular weights in the range from 200 20,000 g/mol.

Additionally or alternatively, the edible composition comprises a film-forming agent. Examples of suitable film-forming agents include water-swellable polymers such as cellulose derived polymers, acrylate-based copolymers, and mixtures thereof, and/or water-soluble polymers such as cellulose derived polymers, homopolymers and copolymers of vinyl alcohols, homopolymers and copolymers of vinyl phenols, homopolymers and copolymers of ethylene oxides, homopolymer and copolymers of maleic acid, collagen, gelatin, alginates, starches, naturally occurring polysaccharides, and mixtures thereof. It is appreciated that the water-swellable polymers are preferably water-insoluble.

Preferably, the water-swellable (and preferably water-insoluble) cellulose derived polymers are selected from cellulose ester polymers such as cellulose acetate, cellulose acetate phthalate, cellulose acetate butyrate, cellulose acetate trimelitate, and hydroxypropylmethyl cellulose phthalate (HPMCP). Preferably, the water-swellable (and preferably water-insoluble) acrylate-based copolymers include anionic, cationic and neutral copolymers. For example, the water-swellable (and preferably water-insoluble) acrylate-based copolymers comprise monomers (and comonomers) selected from acrylic acid, methacrylic acid, methyl acrylate, ethyl acrylate, methyl methacrylate, and ethyl methacrylate. In one preferred embodiment, the water-swellable (and preferably water-insoluble) acrylate-based copolymers include anionic, cationic and neutral copolymers comprising monomers (and comonomers) selected from methacrylic acid, acrylic acid and their derivatives and mixtures thereof.

Preferably, the water-soluble cellulose derived polymers are selected from hydroxypropylcellulose, hydroxyethylcellulose, methylcellulose, hydroxypropyl methylcellulose, carboxymethylcellulose, sodium carboxymethylcellulose, hydratecellulose, and hydroxypropylmethylcellulose. Preferably, the water-soluble naturally occurring polysaccharides are selected from agars, alginates, derivatives of alginic acid, carrageenans, chitin, chitosan, glucomannan, gel Ian gum, gelatin, gum guar, gum Arabic, gum ghatti, gum karaya, gum tragacanth, locust bean gum, pectins, pullulan, starches and starch derivatives, tamarind gum, and xanthans.

Such additive(s) is/are typically well known in the art and the skilled person will only select those additive(s) which is/are considered as being suitable for human beings or animals consumption.

It is appreciated that the edible composition may comprise the one or more additive(s) and its amount in dependence of the edible composition to be prepared and/or the manufacturer's needs. For example, the edible composition may comprise 0.1 to 20 wt.-%, preferably 0.1 to 15 wt.-%, of starches, binding agents; waxes; preservatives; antioxidants; stabilizers or texture modifier; proteins; emulsifier; flavours, artificial sweetener, and/or 20 to 90 wt.-% of sugar(s) and/or polyols, wherein the wt.-% is based on the total weight of the edible composition.

It is preferred that the edible composition comprises 0.1 to 20 wt.-%, preferably 0.1 to 15 wt.-%, emulsifier and/or 20 to 90 wt.-% of sugar(s) and/or polyols, wherein the wt.-% is based on the total weight of the edible composition, and optionally one or more additive(s) selected from the group comprising starches; binding agents; waxes; preservatives; antioxidants; stabilizers or texture modifier, proteins; emulsifier; flavours and artificial sweetener.

In one embodiment, the one or more additive(s) comprises, preferably consists of, one additive. Alternatively, the one or more additive(s) comprises, preferably consists of, two or more additives. For example, the one or more additive(s) comprises, preferably consists of, two or three additives. Preferably, the one or more additive(s) comprises, preferably consists of, one additive.

In one embodiment, the edible composition thus comprises, preferably consists of,
a) water and/or at least one edible oil, preferably water,
b) the surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, and
c) one or more additive(s) selected from the group consisting of starches, such as wheat starch, rice starch, tapioca starch, corn starch, potato starch, pre-gelatinized acetylated distarch adipate and mixtures thereof; binding agents, such as gum arabic, locastbean gum and mixtures thereof; waxes, such as carnauba wax, montan wax and mixtures thereof; preservatives, such as propionic acid, sorbic acid, benzoic acid and salts thereof; antioxidants, such as butylhydroxyanisol (BHA), ascorbic acid, tocopherol, propyl gallate, octyl gallate and mixtures thereof; stabilizers or texture modifier, such as agar agar, gelatin and mixtures thereof; proteins; emulsifier, such as emulsifier comprising sucrose ester or lecithin or sorbitane monostearates and mixtures thereof, flavours, preservatives, artificial sweetener, sugar such as fructose, glucose, sucrose, glucose-fructose mixtures, maltose and mixtures thereof and polyols such as mannitol, sorbitol, xylitol, isomalt, glycerol, maltitol, erythritol, lactitol and mixtures thereof.

In one embodiment, the edible composition comprises, preferably consists of,
a) water and/or at least one edible oil, preferably water,
b) the surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, and
c) 0.1 to 20 wt.-%, based on the total weight of the edible composition, emulsifier.

In an alternative embodiment, the edible composition comprises, preferably consists of,
a) water and/or at least one edible oil, preferably water,
b) the surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, and
c) 0.1 to 20 wt.-%, preferably 0.1 to 15 wt.-%, based on the total weight of the edible composition, emulsifier, and
d) one or more additive(s) selected from the group consisting of starches, such as wheat starch, rice starch, tapioca starch, corn starch, potato starch, pre-gelatinized acetylated distarch adipate and mixtures thereof; binding agents, such as gum arabic, locastbean gum and mixtures thereof; waxes, such as carnauba wax, montan wax and mixtures thereof; preservatives, such as propionic acid, sorbic acid, benzoic acid and salts thereof; antioxidants, such as butylhydroxyanisol (BHA), ascorbic acid, tocopherol, propyl gal late, octyl gallate and mixtures thereof; stabilizers or texture modifier, such as agar agar, gelatin and mixtures thereof; proteins; flavours, preservatives, artificial sweetener, sugar such as fructose, glucose, sucrose, glucose-fructose mixtures, maltose and mixtures thereof and polyols such as mannitol, sorbitol, xylitol, isomalt, glycerol, maltitol, erythritol, lactitol and mixtures thereof.

For example, the edible composition comprises, preferably consists of, a) water and/or at least one edible oil, preferably water,
b) the surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, and
c) 0.1 to 20 wt-%, preferably 0.1 to 15 wt.-%, based on the total weight of the edible composition, emulsifier, and
d) 0.1 to 20 wt.-%, preferably 0.1 to 15 wt.-%, based on the total weight of the edible composition, one or more additive(s) selected from the group consisting of starches, such as wheat starch, rice starch, tapioca starch, corn starch, potato starch, pre-gelatinized acetylated distarch adipate and mixtures thereof; binding agents, such as gum arabic, locastbean gum and mixtures thereof; waxes, such as carnauba wax, montan wax and mixtures thereof; preservatives, such as propionic acid, sorbic acid, benzoic acid and salts thereof; antioxidants, such as butylhydroxyanisol (BHA), ascorbic acid, tocopherol, propyl gallate, octyl gallate and mixtures thereof; stabilizers or texture modifier, such as agar agar, gelatin and mixtures thereof; proteins; flavours, preservatives, artificial sweetener, and/or
e) 20 to 90 wt.-%, based on the total weight of the edible composition, sugar such as fructose, glucose, sucrose, glucose-fructose mixtures, maltose and mixtures thereof and/or polyols such as mannitol, sorbitol, xylitol, isomalt, glycerol, maltitol, erythritol, lactitol and mixtures thereof.

It is appreciated that the total amount of the components in the edible composition amounts to 100 wt-%, based on the total weight of the edible composition.

The edible composition may further comprise at least one natural ground calcium carbonate (NGCC) and/or at least one precipitated calcium carbonate (PCC).

For example, the edible composition further comprises at least one natural ground calcium carbonate (NGCC).

For example, the at least one natural ground calcium carbonate (NGCC) is a wet ground natural calcium carbonate.

GCC is understood to be a naturally occurring form of calcium carbonate, mined from sedimentary rocks such as limestone or chalk, or from metamorphic marble rocks and processed through a treatment such as grinding, screening and/or fractionizing in wet form, for example by a cyclone or classifier. In one embodiment of the present invention, the NGCC is selected from the group comprising marble, chalk, dolomite, limestone and mixtures thereof.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

For example, the at least one natural ground calcium carbonate (NGCC) is marble, more preferably a wet ground marble.

It is appreciated that the amount of calcium carbonate in the at least one natural ground calcium carbonate (NGCC) and/or at least one precipitated calcium carbonate (PCC) is at least 80 wt.-%, e.g. at least 95 wt.-%, preferably between 97 and 100 wt. %, more preferably between 98.5 and 99.95 wt.-%, based on the total dry weight of the at least one natural ground calcium carbonate (NGCC) and/or at least one precipitated calcium carbonate (PCC).

The at least one natural ground calcium carbonate (NGCC) and/or at least one precipitated calcium carbonate (PCC) is preferably in the form of a particulate material, and may have a particle size distribution as conventionally employed for the material(s) involved in the type of product to be produced. In general, it is preferred that the at least one natural ground calcium carbonate (NGCC) and/or at least one precipitated calcium carbonate (PCC) has/have a weight median particle size $d_{50}$ from 0.05 to 100 μm, more preferably from 0.1 to 75 μm, even more preferably from 0.25 to 50 μm, and most preferably from 0.5 to 40 μm.

It is preferred that the at least one natural ground calcium carbonate (IGCC) and/or at least one precipitated calcium carbonate (PCC) has/have a top cut ($d_{98}$) of ≤80 μm. For example, the at least one ground calcium carbonate-comprising filler material has a top cut ($d_{98}$) of ≤35 μm, preferably of ≤25 μm, more preferably of ≤15 μm and most preferably of ≤12 μm.

In one embodiment, the at least one natural ground calcium carbonate (NGCC) and/or at least one precipitated calcium carbonate (PCC) is preferably at least one natural ground calcium carbonate (NGCC).

It is appreciated that the amount of the at least one natural ground calcium carbonate (NGCC) and/or at least one precipitated calcium carbonate (PCC), if present, is preferably above the amount of the surface-reacted calcium carbonate.

According to one embodiment, the edible composition thus comprises, preferably consists of, a) water and/or at least one edible oil, preferably water,
b) the surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, and
c) at least one natural ground calcium carbonate (NGCC) and/or at least one precipitated calcium carbonate (PCC), preferably at least one natural ground calcium carbonate (NGCC).

In an alternative embodiment, the edible composition comprises, preferably consists of,
a) water and/or at least one edible oil, preferably water,
b) the surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
c) one or more additive(s) selected from the group consisting of icing sugar, starches, such as wheat starch, rice starch, tapioca starch, corn starch, potato starch, pre-gelatinized acetylated distarch adipate and mixtures thereof; binding agents, such as gum arabic, locastbean gum and mixtures thereof; waxes, such as carnauba wax, montan wax and mixtures thereof; preservatives, such as propionic acid, sorbic acid, benzoic acid and salts thereof; antioxidants, such as butylhydroxyanisol (BHA), ascorbic acid, tocopherol, propyl gallate, octyl gallate and mixtures thereof; stabilizers or texture modifier, such as agar agar, gelatin and mixtures thereof; proteins; emulsifier, such as emulsifier comprising sucrose ester or lecithin or sorbitane monostearates and mixtures thereof, flavours, preservatives, artificial sweetener, sugar such as fructose, glucose, sucrose, glucose-fructose mixtures, maltose and mixtures thereof, and polyols such as mannitol, sorbitol, xylitol, isomalt, glycerol, maltitol, erythritol, lactitol and mixtures thereof, and
d) at least one natural ground calcium carbonate (NGCC) and/or at least one precipitated calcium carbonate (PCC), preferably at least one natural ground calcium carbonate (NGCC).

The edible composition may be in the form of any composition which can be coated onto and/or filled into a food product or pharmaceutical product or neutraceutical product. According to one embodiment of the present invention, the edible composition is thus selected from a food coating, sugar coating, sugar-free coating, nutra coating, food decoration, food filling, pharmaceutical coating and the like, and mixtures thereof.

Edible Coating and/or Filling and Further Products

According to a further aspect, an edible coating and/or filling comprising a surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

With regard to the definition of the surface-reacted calcium carbonate and preferred embodiments thereof, reference is made to the statements provided above when discussing the technical details of the edible composition of the present invention.

It is appreciated that the edible coating and/or filling is obtained from the edible composition described herein.

As regards the edible coating, it is preferred that it is obtained by applying the edible composition, as defined herein, on the product to be coated and drying the edible composition. Accordingly, the edible coating preferably has a content of water and/or at least one oil which is below the water and/or oil content of the edible composition.

However, the final content of water and/or the at least one oil depend on the product to be prepared and/or the manufacturer's equipment, and thus may vary over a broad range.

Preferably, the content of water and/or the at least one oil in the edible coating is in the range from 1.0 to 70.0 wt.-%, based on the total weight of the edible coating, preferably from 1.5 to 50.0 wt.-%, more preferably from 2.0 to 30.0 wt.-%, and most preferably from 2.5 to 25.0 wt.-%.

As already mentioned above, the edible coating is preferably obtained from the edible composition. Accordingly, the edible coating may further comprise one or more additive(s) and/or at least one natural ground calcium carbonate (NGCC) and/or at least one precipitated calcium carbonate (PCC).

With regard to the definition of the one or more additive(s), the at least one natural ground calcium carbonate (NGCC), the at least one precipitated calcium carbonate (PCC) and preferred embodiments thereof, reference is made to the statements provided above when discussing the technical details of the edible composition of the present invention.

As the edible coating is preferably obtained by applying the edible composition on the product to be coated and drying the edible composition, the contents of the one or more additive(s) and/or at least one natural ground calcium carbonate (NGCC) and/or at least one precipitated calcium carbonate (PCC) in the edible coating is above their respective contents in the edible composition.

Additionally or alternatively, an edible filling is obtained from the edible composition.

It is preferred that the edible filling is obtained by filling the edible composition, as defined herein, into a product to be filled and optionally drying the edible composition. Accordingly, the filling preferably has a content of water and/or at least one oil that is similar or below the water and/or oil content of the edible composition.

However, the final content of water and/or the at least one oil depend on the product to be prepared and/or the manufacturer's equipment, and thus may vary over a broad range.

Preferably, the content of water and/or the at least one oil in the edible filling is in the range from 1.0 to 70.0 wt.-%, based on the total weight of the edible coating, preferably from 1.5 to 50.0 wt.-%, more preferably from 2.0 to 40.0 wt.-% and most preferably from 5.0 to 30.0 wt.-%.

As already mentioned above, the edible filling is preferably obtained from the edible composition. Accordingly, the edible filling may further comprise one or more additive(s) and/or at least one natural ground calcium carbonate (NGCC) and/or at least one precipitated calcium carbonate (PCC).

With regard to the definition of the one or more additive(s), the at least one natural ground calcium carbonate (NGCC), the at least one precipitated calcium carbonate (PCC) and preferred embodiments thereof, reference is made to the statements provided above when discussing the technical details of the edible composition of the present invention.

As the edible filling is preferably Obtained by filling the edible composition into the product to be filled and optionally drying the edible composition, the contents of the one or more additive(s) and/or at least one natural ground calcium carbonate (NGCC) and/or at least one precipitated calcium carbonate (PCC) in the edible filling is similar or above their respective contents in the edible composition.

It is appreciated that the edible composition is preferably at least partially coated onto and/or filled into a food product or pharmaceutical product or neutraceutical product.

In a further aspect, the present invention thus refers to a food product or pharmaceutical product or neutraceutical product at least partially coated and/or filled with the edible composition, as defined herein.

With regard to the definition of the edible composition and preferred embodiments thereof, reference is made to the statements provided above when discussing the technical details of the edible composition of the present invention.

The term "food product" in the meaning of the present invention refers to a nourishment that is eaten to sustain life, provide energy or promote growth.

For example, the food product is selected from cakes, cookies, candies, cereals, cereal bars, chips, chewing gum, ice cream wafer and the like.

The term "pharmaceutical product" in the meaning of the present invention refers to a solid product that is manufactured for providing a medicinal drug.

For example, the pharmaceutical product is selected from tablets, mini-tables, pellets, capsules, granules and the like.

The term "neutraceutical product" in the meaning of the present invention refers to a solid product that is manufactured for providing a nutritional compound.

For example, the neutraceutical product is selected from tablets, mini-tables, pellets, capsules, granules and the like.

Methods and Uses

The present invention further refers in another aspect to a method for producing a food product or pharmaceutical product or neutraceutical product at least partially coated and/or filled with the edible composition.

The method comprises the steps of
a) mixing water and/or at least one edible oil with a surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, for obtaining an edible composition, and
b) applying the edible composition obtained in step a), one or more times, at least partially on the surface of a food product or pharmaceutical product or neutraceutical product, or filling the edible composition obtained in step a) into a food product or pharmaceutical product or neutraceutical product.

With regard to the definition of the edible composition, the surface-reacted calcium carbonate, water, the at least one edible oil and preferred embodiments thereof, reference is made to the statements provided above when discussing the technical details of the edible composition of the present invention.

The surface-reacted calcium carbonate may be provided in any suitable liquid or dry form. For example, the surface-reacted calcium carbonate may be in form of a powder and/or a suspension. The suspension can be obtained by mixing the surface-reacted calcium carbonate with a solvent, preferably water. The surface-reacted calcium carbonate to be mixed with a solvent, and preferably water, may be provided in any form, for example, as suspension, slurry, dispersion, paste, powder, a moist filter cake or in pressed or granulated form.

As the surface-reacted calcium carbonate is mixed with water and/or the at least one edible oil in step a), it is advantageous to provide the surface-reacted calcium carbonate as concentrated as possible, i.e. the water content should be as low as possible, in order to avoid an excessive dilution in step a). Thus, the surface-reacted calcium carbonate is preferably provided as a powder. In an alternative embodiment, the surface-reacted calcium carbonate is provided in form of a suspension and then mixed with water and/or the at least one edible oil.

In case the surface-reacted calcium carbonate is provided in dry form, the moisture content of the surface-reacted calcium carbonate can be between 0.01 and 5 wt.-%, based on the total weight of the surface-reacted calcium carbonate. The moisture content of the surface-reacted calcium carbonate can be, for example, less than or equal to 1.0 wt.-%, based on the total weight of the surface-reacted calcium carbonate, preferably less than or equal to 0.5 wt.-%, and more preferably less than or equal to 0.2 wt.-%. According to another example, the moisture content of the surface-reacted calcium carbonate may be between 0.01 and 0.15 wt.-%, preferably between 0.02 and 0.10 wt.-%, and more preferably between 0.03 and 0.07 wt.-%, based on the total weight of the surface-reacted calcium carbonate.

The mixing of the water and/or the at least one edible oil and the surface-reacted calcium carbonate may be carried out in any manner known by the skilled person.

The mixing may be carried out under conventional mixing conditions. The skilled man will adapt these mixing conditions (such as the configuration of mixing pallets and mixing speed) according to his process equipment. It is appreciated that any mixing method which would be suitable to form an edible composition may be used.

Step a) is carried out such that the edible composition obtained in step a) has a solids content, i.e. the surface-reacted calcium carbonate, in an amount from 1.0 to 50.0 wt.-%, based on the total weight of the edible composition, preferably from 1.5 to 25.0 wt.-%, more preferably from 2.0 to 15.0 wt.-% and most preferably from 2.5 to 12.0 wt.-%.

In case, the method comprises the mixing of water and at least one oil and the surface-reacted calcium carbonate, the mixing may be carried out in any order. Preferably, the water and the at least one oil are combined and mixed to form a mixture followed by the addition and mixing of the surface-reacted calcium carbonate.

Mixing can be carried out at temperatures typically used for preparing an edible composition. Preferably, mixing is carried out at a temperature in the range from 15 to 100° C., more preferably from 20 to 85° C. and most preferably from 20 to 70° C., such as from 20 to 45° C.

The method for producing a food product or pharmaceutical product or neutraceutical product at least partially coated and/or filled with the edible composition may further comprise the provision of one or more additive(s) and/or at least one natural ground calcium carbonate (NGCC) and/or at least one precipitated calcium carbonate (PCC). The combining and mixing of the one or more additive(s) and/or at least one natural ground calcium carbonate (NGCC) and/or at least one precipitated calcium carbonate (PCC), water and/or the at least one edible oil and the surface-reacted calcium carbonate may also be carried out under conventional mixing conditions. The skilled man will adapt these mixing conditions (such as the configuration of mixing pallets and mixing speed) according to his process equipment. It is appreciated that any mixing method which would be suitable to form an edible composition may be used.

In case, the method comprises the provision of the surface-reacted calcium carbonate, water and/or at least one oil, and one or more additive(s) and/or at last one natural ground calcium carbonate (NGCC) and/or at least one precipitated calcium carbonate (PCC), the combining and mixing may be carried out in any order.

In step b) of the present method, the edible composition obtained in step a) is applied (or coated), one or more times, at least partially on the surface of a food product or pharmaceutical product or neutraceutical product. Alternatively, the edible composition obtained in step a) is filled, one or more times, into a food product or pharmaceutical product or neutraceutical product.

Applying (or coating) the edible composition at least partially on the surface of a food product or pharmaceutical product or neutraceutical product can be carried out by any means known in the art to be suitable for spreading a composition at least partially on the surface of a food product or pharmaceutical product or neutraceutical product. The skilled man will adapt the application/coating conditions (such as the amount or coating speed) according to his process equipment.

For example, applying the edible composition at least partially on the surface of a food product or pharmaceutical product or neutraceutical product in step b) is carried out by brushing or pouring, pan coating, curtain or dip coating, fluidized bed coating, hot melt coating and/or compression coating.

These methods are well known in the art and do not need to be described in more detail in the present application.

Alternatively, the edible composition obtained in step a) is filled into a food product or pharmaceutical product or neutraceutical product.

Filling the edible composition into a food product or pharmaceutical product or neutraceutical product can be carried out by any means known in the art to be suitable for filling a composition into a food product or pharmaceutical product or neutraceutical product. The skilled man will adapt the filing conditions (such as the amount or filling speed) according to his process equipment.

For example, filling the edible composition into a food product or pharmaceutical product or neutraceutical product in step b) is carried Out by injecting the edible composition into the food product or pharmaceutical product or neutraceutical product.

These methods are well known in the art and do not need to be described in more detail in the present application.

It is appreciated that application or filling step b) is carried out one or more times, preferably one time. That is to say, if application or filling step b) is carried out more times, step b) can be repeated one or more times.

In one embodiment, the method further comprises a step c) of drying the edible composition applied (or coated) onto or filled into the food product or pharmaceutical product or neutraceutical product. Preferably step c) is applied if the edible composition is applied (or coated) onto the food product or pharmaceutical product or neutraceutical product.

Drying of the edible composition can be carried out by any means known in the art to be suitable for drying a food product or pharmaceutical product or neutraceutical product. The skilled man will adapt the drying conditions (such as the stream of air or heat) according to his process equipment.

For example, drying of the edible composition in or onto the food product or pharmaceutical product or neutraceutical product in step c) is carried out by air drying or by using heat or a stream of air.

It is thus appreciated that the edible composition applied (or coated) onto or filled into the food product or pharmaceutical product or neutraceutical product and dried, comprises a less amount of water than the edible composition previously applied onto or filled into the product.

The scope and interest of the invention will be better understood based on the following examples which are intended to illustrate certain embodiments of the present invention and are non-limitative.

SHORT DESCRIPTION OF THE FIGURES

EXAMPLES

1. Measurement Methods

Figure 1:
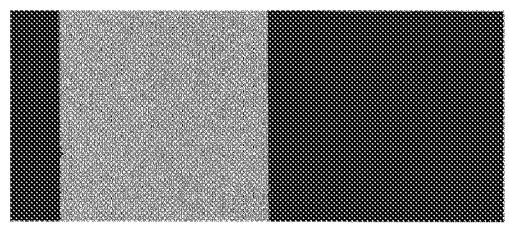
FIG. 1 shows the coveting power of an icing sugar only (reference)
Figure 2:
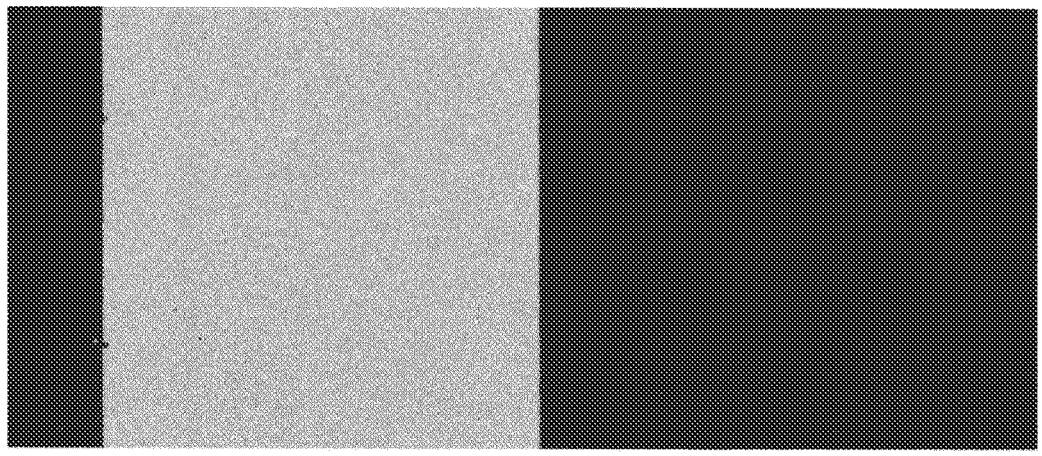
FIG. 2 shows the covering power of a sugar coating comprising 0.5 wt.-% titanium dioxide (Formulation 9, reference)
Figure 3:
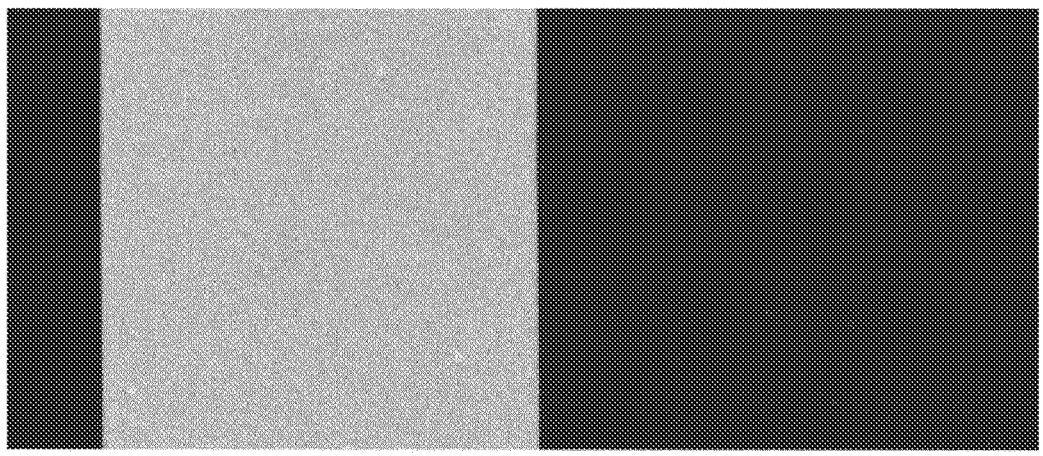
FIG. 3 shows the coveting power of a sugar coating comprising 35 wt.-% natural ground calcium carbonate (NGCC) (Formulation 13, reference)
Figure 4:
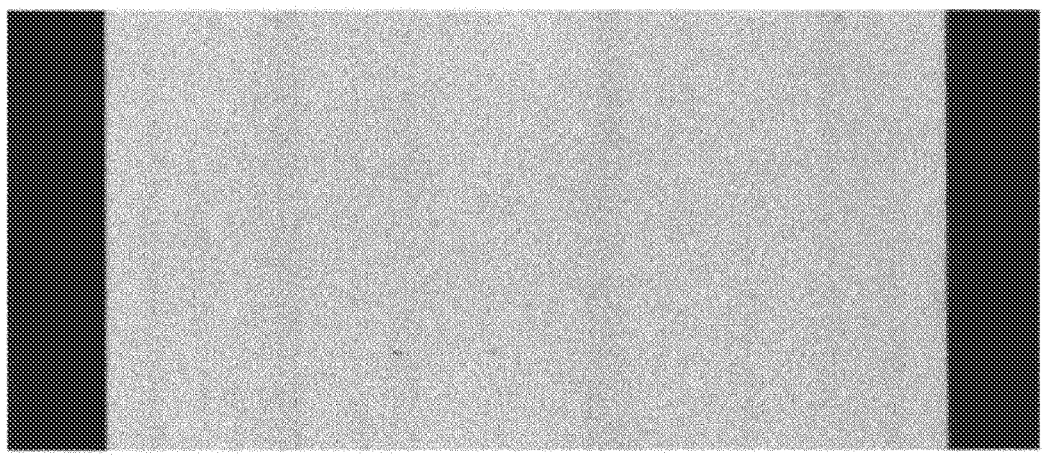
FIG. 4 shows the covering power of a sugar coating comprising 8 wt.-% surface-reacted calcium carbonate (Formulation 15)
Figure 5:
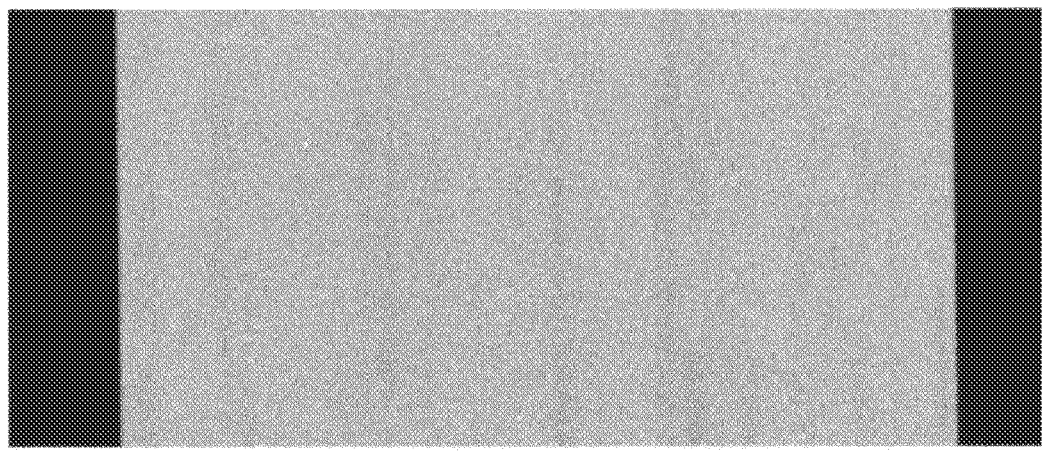
FIG. 5 shows the covering power of a sugar coating comprising 4 wt.-% surface-reacted calcium carbonate (Formulation 17)

In the following, measurement methods implemented in the examples are described.

Particle Size Distribution

Volume determined median particle size $d_{50}(vol)$ and the volume determined top cut particle size $d_{98}(vol)$ was evaluated using a Malvern Mastersizer 2000 Laser Diffraction System Malvern Instruments Plc., Great Britain). The $d_{50}$(vol) or $d_{98}(vol)$ value indicates a diameter value such that 50% or 98% by volume, respectively, of the particles have a diameter of less than this value. The raw data obtained by the measurement was analyzed using the Mie theory, with a particle refractive index of 1.57 and an absorption index of 0.005. The methods and instruments are known to the skilled person and are commonly used to determine particle size distributions of fillers and pigments.

The weight determined median particle size $d_{50}(wt)$ was measured by the sedimentation method, which is an analysis of sedimentation behaviour in a gravimetric field. The measurement was made with a Sedigraph™ 5120 of Micromeritics Instrument Corporation, USA. The method and the instrument are known to the skilled person and are commonly used to determine particle size distributions of fillers and pigments. The measurement was carried out in an aqueous solution of 0.1 wt.-% $Na_4P_2O_7$. The samples were dispersed using a high speed stirrer and supersonicated.

Specific Surface Area (SSA)

The specific surface area was measured via the BET method according to ISO 9277 using nitrogen, following conditioning of the sample by heating at 250° C. for a period of 30 minutes. Prior to such measurements, the sample was filtered within a Büchner funnel, rinsed with deionised water and dried overnight at 90 to 100° C. in an oven. Subsequently, the dry cake was ground thoroughly in a mortar and the resulting powder was placed in a moisture balance at 130° C. until a constant weight was reached.

Intra-Particle Intruded Specific Pore Volume (in cm³/g)

The specific pore volume was measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm(~nm). The equilibration time used at each pressure step was 20 seconds. The sample material was sealed in a 5 cm³ chamber powder penetrometer for analysis. The data were corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi-modal, and by taking the specific pore volume intruded by mercury into pores finer than the modal turning point, i.e. finer than the bi-modal point of inflection, the specific intra-particle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preparation of a Coated Surface

Coated surfaces were prepared by using the respective coating formulations and applying them with a box scarper having a coater gap of 300 μm on contrast cards. The contrast cards used are Leneta contrast cards, form 3-B-H, size 7⅝×11⅜ (194×289 mm), sold by the company Leneta, and distributed by Novamart, Stäfa, Switzerland.

Determination of Colour Values (Rx, Ry, Rz)

The colour values Rx, Ry, Rz were determined over the white and black fields of the Leneta contrast card, and are measured with a spectraflas SF 450×spectrophotometer of the company Datacolor, Montreuil, France.

Contrast Ratio (Opacity) of a Coated Surface/Film

Contrast ratio (covering power) values were determined according to ISO 2814 at a spreading rate of 7.5 m²/l with the ELREPHO SF 450X.

The contrast ratio was calculated as described by the equation below:

$$\text{Contrast ratio } [\%] = \frac{Ry_{black}}{Ry_{white}} \times 100\%$$

with $Ry_{black}$ and $Ry_{white}$ being obtained by the measurement of the color values.

Yellowness Value

The yellowness value was determined according to ISO 2814 at a spreading rate of 7.5 m²/l with the ELREPHO SF 450X.

Dry Film Thickness

The film was allowed to dry and then the thickness of the film was measured with a L&W micrometer, Lorentzen & Wettre.

2. MATERIALS

Pigment Materials
Titanium Dioxide
Tioxide® Purity 73 was obtained from Huntsman.
Calcium Carbonate
GCC 1: a high purity natural calcium carbonate having a $d_{50}$ (wt.-%) of 2 μm that is commercially available from Omya
GCC 2: a high purity natural calcium carbonate having a $d_{50}$ (wt.-%) of 3 μm that is commercially available from Omya
GCC 3: a high purity natural calcium carbonate having a $d_{50}$ (wt.-%) of 5.5 μm that is commercially available from Omya
Surface-Reacted Calcium Carbonate
SRCC 1
SRCC1 has a $d_{50}$=6.6 μm, a $d_{98}$=13.7 μm, a SSA=59.9 $m^2g^{-1}$ and an intra-particle intruded specific pore volume of 0.939 cm³/g (for the pore diameter range of 0.004 to 0.51 μm).

The SRCC 1 has been prepared as follows:

SRCC 1 was obtained by preparing 350 litres of an aqueous suspension of ground calcium carbonate in a mixing vessel by adjusting the solids content of a ground limestone calcium carbonate from Omya SAS, Orgon having a mass based median particle size of 1.3 μm, as determined by sedimentation, such that a solids content of 10 wt.-%, based on the total weight of the aqueous suspension, is obtained.

Whilst mixing the slurry at a speed of 6.2 m/s, 11.2 kg phosphoric acid was added in form of an aqueous solution containing 30 wt.-% phosphoric acid to said suspension over a period of 20 minutes at a temperature of 70° C. After the addition of the acid, the slurry was stirred for additional 5 minutes, before removing it from the vessel and drying using a jet-dryer.

SRCC 2

SRCC 2 had a $d_{50}(vol)$=6.2 μm, $d_{98}(vol)$=9.7 μm, SSA=88.0 m²/g with an intra-particle intruded specific pore volume of 1.550 cm³/g (for the pore diameter range of 0.004 to 0.6 μm).

The SRCC 2 has been prepared as follows:

In a mixing vessel, 10 liters of an aqueous suspension of ground marble calcium carbonate was prepared by adjusting the solids of a ground marble calcium carbonate having a particle size distribution of 90 wt.-% below 2 μm, based on the total weight of the ground calcium carbonate, such that a solids content of 15 wt.-%, based on the total weight of the aqueous suspension, is obtained.

Whilst mixing the slurry, 2.8 kg phosphoric acid was added in form of an aqueous solution containing 30 wt.-% phosphoric acid to said suspension over a period of 10 minutes. Throughout the whole experiment the temperature of the suspension was maintained at 70° C. After the addition of the acid, the suspension was stirred for additional 5 minutes before removing it from the vessel and drying.

SRCC 3

SRCC 3 had $d_{50}(vol)=4.5$ μm, $d_{98}(vol.)=8.6$ μm, SSA=96.1 m$^2$/g with an intra-particle intruded specific pore volume of 1.588 cm$^3$/g (for the pore diameter range of 0.004 to 0.4 μm).

The SRCC 3 has been prepared as follows:

In a mixing vessel, 10 liters of an aqueous suspension of ground limestone calcium carbonate was prepared by adjusting the solids of a ground limestone calcium carbonate having a particle size distribution of 90 wt.-% below 2 μm, based on the total weight of the ground calcium carbonate, such that a solids content of 15 wt.-%, based on the total weight of the aqueous suspension, is obtained.

Whilst mixing the slurry, 2.8 kg phosphoric acid was added in form of an aqueous solution containing 30 wt.-% phosphoric acid to said suspension over a period of 10 minutes. Throughout the whole experiment the temperature of the suspension was maintained at 70° C. After the addition of the acid, the suspension was stirred for additional 5 minutes before removing it from the vessel and drying.

Other Materials

Tween 60V Pharma (emulsifier): is a Polysorbate 60: polyoxyethylene (20) sorbitan monostearate; an emulsifier used in pharma and food preparations. The supplier was Croda.

Icing sugar: powdered sugar; obtained from Migros, Switzerland under the name "poudre".

Chewing gum cores: supplied by asCom Confection GmbH, Walldorf, Germany; sugar-free and containing sorbitol, maltitol syrup and mannitol. The average weight of each gum core was 1.5 grams.

Crystal sugar: supplied by Suedzucker, Germany.

Sugar alcohol maltitol: supplied by Roquette under the name "Maltisorb P200".

PEG 6005 (plasticizers: supplied by BASF AG, Germany, is a polyethylene glycol) having a molecular weight from 570 to 630 g/mol Pharmacoat 606 (film-forming agent): supplied by Shin-Etsu Chemical Co., Ltd., Japan, and is a hydroxypropyl methylcellulose (HPMC) grade 606, substitution type 2910, i.e. the first two digits indicate the percentage of methoxy groups; last two digits indicate the percentage of hydroxypropyl groups, having a viscosity of 6 mPas/s.

Dimethicone grade: defoaming agent): supplied by Solvias AG, Switzerland.

Sodium lauryl sulphate (SLS: surfactant): supplied by Sigma-Aldrich, USA.

3. EXAMPLES

A. Preparation of Sugar Coating Formulations

The coating formulations were produced according to the following protocol.

1. Preparation of Tween 60V Pharma Solution and Pigment Material Pastes Used

Before preparing the final coating formulations, a paste containing only the pigment material, water and emulsifier (polyoxyethylene (20) sorbitan monostearate; Tween 60 V Pharma) has been produced in order to disperse the pigment material particles and to avoid the formation of agglomerates.

The below Table 1 shows an overview over the emulsifier solution and pigment material pastes produced:

TABLE 1

Emulsifier solution and pigment material pastes

| Ingredient | | | | | % w/w | | | | |
|---|---|---|---|---|---|---|---|---|---|
| | Formula | 0 | 1 | 2 | 3 | 4 | 5 | 6 | 7 |
| A) | Aqua dem. | 75.0 | 32.0 | 23.0 | 23.0 | 21.0 | 58.6 | 67.3 | 69.4 |
| | Emulsifier | 25.0 | 6.0 | 4.5 | 4.5 | 4.5 | 11.0 | 11.5 | 11.8 |
| | TiO$_2$ | — | 55.0 | — | — | — | — | — | — |
| | GCC 1 | — | — | 71.4 | — | — | — | — | — |
| | GCC 2 | — | — | — | 71.4 | — | — | — | — |
| | GCC 3 | — | — | — | — | 74.1 | — | — | — |
| | SRCC 1 | — | — | — | — | — | 30.4 | — | — |
| | SRCC 2 | — | — | — | — | — | — | 21.2 | — |
| | SRCC 3 | — | — | — | — | — | — | — | 18.8 |
| B) | Aqua dem. | — | 7.0 | 1.1 | 1.1 | 3.1 | — | — | — |
| | | 100 | 100 | 100 | 100 | 100 | 100 | 100 | 100 |
| | | Emulsifier solution | TiO$_2$ paste | GCC 1 paste | GCC 2 paste | GCC 3 paste | SRCC 1 paste | SRCC 2 paste | SRCC 3 paste |

Phase A

In a container water and emulsifier were blended with a Dispermat™ (from Getzmann, Reichshof, Germany) using the dissolver impeller with a diameter of 40 mm.

Then, the pigment material was slowly added, and the resulting mixture was mixed using the Dispermat™ (4 000 rpm; appr. 5 minutes, dissolver impeller diameter: 40 mm) until a homogenous mixture was obtained.

Phase B

Then, the water (phase B) was added at, the end to phase A and mixed by hand.

The quantity of produced paste was 500 g for each case.

Remark: The emulsifier was added in order to improve the wetting and the homogeneity of the pigment material used.

2. Preparation of Final Coating Formulations

Phase C

In a container water and emulsifier or emulsifier solution prepared according to Formula 0 listed in Table 1 were blended with a Dispermat™ (from Getzmann, Reichshof, Germany) using the dissolver impeller with a diameter of 40 mm.

Then, the pigment material paste (listed in Formulas 1 to 7 of Table 1) was slowly added, and the resulting mixture was mixed using the Dispermat™ (4 000 rpm; appr. 5 minutes, dissolver impeller diameter: 40 mm) until a homogenous mixture was obtained.

Phase D

The components of phase D were added after the homogenization of phase C in the following order:

The icing sugar was slowly added to phase C and mixed under high/medium speed using the Dispermat™ (4 000 rpm, 5-10 minutes, dissolver impeller diameter: 40 mm)

Then, the water was added at the end and mix by hand.

The quantity of produced final coating formulation was 100 g for each case.

After mixing and before spreading on the Leneta contrast cards, the final icing sugar coating formulation has been mixed for 2 minutes at 3 000 rpm using a SpeedMixer™ DAC 150.1 FVZ (from Hauschild, Hamm, Germany).

The below Table 2 shows an overview over the produced final coating formulations and lists all of the components used as well as their quantities.

Finally, Table 4 shows the R(y) white part and R(y) black part as well as the covering power (in %) that was measured for the final coating formulations listed in Table 2.

TABLE 4

Covering power (in %) and R(y) white part and R(y) black part for the produced final coating formulations

| Formula | R(y) white part | R(y) black part | Covering power (%) |
|---|---|---|---|
| 8 | 85.5 | 28.6 | 33.4 |
| 9 | 85.6 | 41.2 | 48.2 |
| 10 | 84.9 | 28.3 | 33.3 |
| 11 | 85.0 | 33.6 | 39.5 |
| 12 | 85.0 | 41.2 | 48.5 |
| 13 | 85.3 | 39.5 | 48.7 |
| 14 | 85.6 | 41.3 | 48.2 |
| 15 | 84.3 | 40.1 | 47.6 |
| 16 | 84.9 | 36.2 | 42.6 |
| 17 | 84.5 | 36.5 | 43.1 |
| 18 | 85.0 | 46.1 | 54.2 |

TABLE 2

Quantities of components used in the final coating formulations

| Ingredients | | % w/w | | | | | | | | | |
|---|---|---|---|---|---|---|---|---|---|---|---|
| Formula | 8 | 9 | 10 | 11 | 12 | 13 | 14 | 15 | 16 | 17 | 18 |
| C) Aqua dem. | 7.2 | 1.0 | 4.0 | 4.0 | 2.5 | 2.5 | 2.0 | 1.4 | 0.9 | 2.0 | — |
| Emulsifier | — | — | 2.5 | 1.9 | 1.0 | 1.0 | 0.6 | 0.3 | 0.5 | 0.7 | — |
| Emulsifier solution (Formula 0) | 12.8 | 12.4 | — | — | — | — | — | — | — | — | — |
| $TiO_2$ Paste (Formula 1) | — | 0.9 | — | — | — | — | — | — | — | — | — |
| GCC 1 Paste (Formula 2) | — | — | 14.0 | 28.0 | 49.0 | — | — | — | — | — | — |
| GCC 2 Paste (Formula 3) | — | — | — | — | — | 49.0 | — | — | — | — | 31.0 |
| GCC 3 Paste (Formula 4) | — | — | — | — | — | — | 56.0 | — | — | — | — |
| SRCC 1 Paste (Formula 5) | — | — | — | — | — | — | — | 26.3 | — | — | 16.4 |
| SRCC 2 Paste (Formula 6) | — | — | — | — | — | — | — | — | 23.60 | — | — |
| SRCC 3 Paste (Formula 7) | — | — | — | — | — | — | — | — | — | 21.30 | — |
| D) Icing sugar | 80.0 | 79.5 | 70.0 | 60.0 | 45.0 | 45.0 | 40.0 | 72.0 | 75.0 | 76.0 | 52.6 |
| Aqua dem. | — | 6.2 | 9.5 | 6.1 | 2.5 | 2.5 | 1.4 | — | — | — | — |
| | 100 | 100 | 100 | 100 | 100 | 100 | 100 | 100 | 100 | 100 | 100 |

The following Table 3 gives an overview over the amount of pigment material that was present in the final coating formulations shown in Table 2.

TABLE 3 amount of pigment material present in the final coating formulations

| Formula | 9 | 10 | 11 | 12 | 13 | 14 | 15 | 16 | 17 | 18 |
|---|---|---|---|---|---|---|---|---|---|---|
| $TiO_2$ (%) | 0.5 | — | — | — | — | — | — | — | — | — |
| GCC 1 (%) | — | 10.0 | 20.0 | 35.0 | — | — | — | — | — | — |
| GCC 2 (%) | — | — | — | — | 35.0 | — | — | — | — | 22.2 |
| GCC 3 (%) | — | — | — | — | — | 40.0 | — | — | — | — |
| SRCC 1 (%) | — | — | — | — | — | — | 8.0 | — | — | 5.0 |
| SRCC 2 (%) | — | — | — | — | — | — | — | 5.0 | — | — |
| SRCC 3 (%) | — | — | — | — | — | — | — | — | 4.0 | — |

From the above results it is apparent that surface-reacted calcium carbonates provide a similar coverage to sugar coatings containing 20 to 40 wt.-% of ground calcium carbonates (Formulation Nos. 11 to 13) but at lower concentrations (8 wt.-%, 5 wt.-% and 4 wt.-% for Formulation Nos. 14 to 16, respectively).

Also, the surface-reacted calcium carbonates provide a similar coverage to a sugar coating containing titanium dioxide. The best covering was obtained with a mixture of a ground calcium carbonate and a surface-reacted calcium carbonate, and this covering was even better than the one provided by titanium dioxide.

The results are also shown in FIGS. 1 to 5, showing the covering power icing sugar only and formulations 9, 12, 15 and 17.

B. Coating of Chewing Gum Cores with a Coating Formulation

The present example exemplifies the coating of chewing gum cores with different sugar/polyol and mineral material formulations.

Also, the coating strength and the coating thickness of the obtained coated chewing gums was determined.

Coating of Chewing Gum Cores with Coating Formulations

The coating of the gum cores was carried out in a standard coating pan with a batch size of 10 kg.

The formulations used for coating of the gum cores are listed in following Table 5.

Measurement of the Coating Strength and the Coating Thickness

Figure 8:
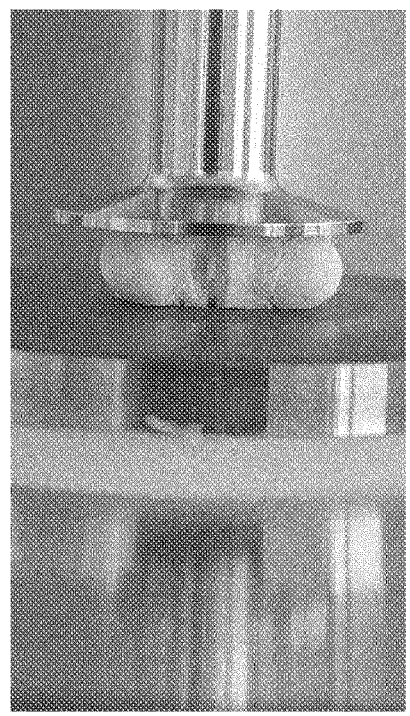
FIG. 8 shows the breaking of a chewing gum coating
Figure 9:
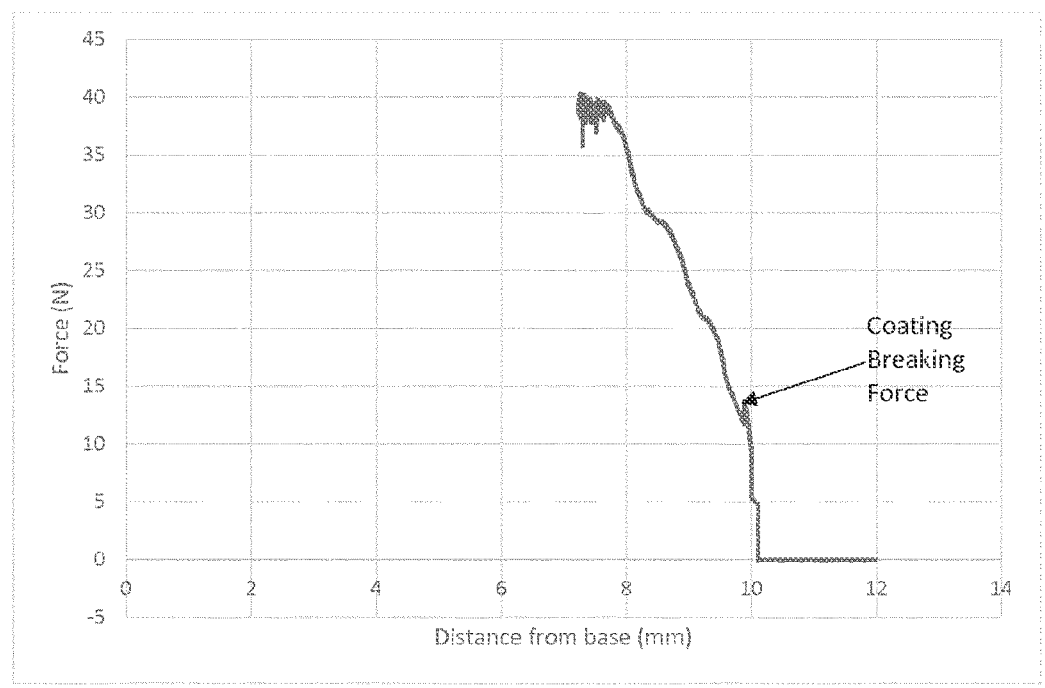
FIG. 9 shows a typical graph as generated by the testing method for breaking of a chewing gum coating

The coating strength was measured using an Anton Paar MCR 301 rheometer instrument. The geometry plate was moved with a constant speed of 0.1 mm/sec and the force was measured while pressing the chewing gum dragee (FIG. 8). The force was recorded every 5 micrometer of movement and every 0.5 sec. A typical graph of the measurement is shown in FIG. 9. In the graph, the distance of geometry from the base in millimeters (mm) is shown on the x-axis and the recorded force in newton (N) is shown on the y-axis.

The thickness of the chewing gum coating was calculated by difference between height of coated chewing gum core and uncoated chewing gum cores. The strength of coating was determined by the point in measurement graph where there was sudden dip into the force, this was due to the breakage of chewing gum coating (FIG. 9)

Figure 10:
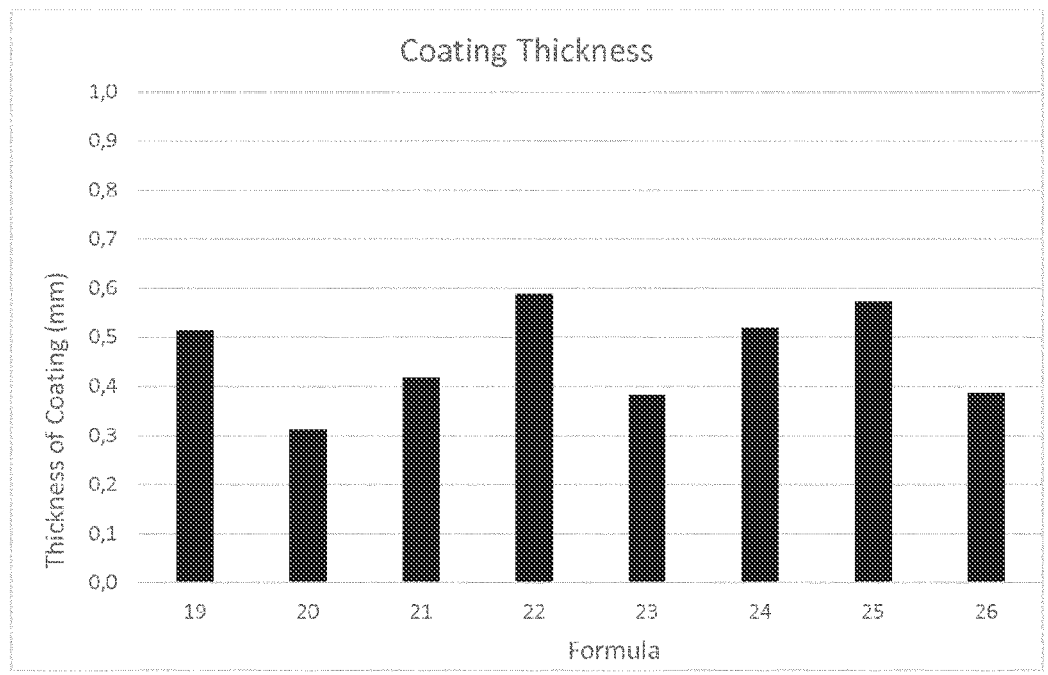
FIG. 10 shows the influence of coating thickness on chewing gum cores

As seen clearly in FIG. 10, the influence of SRCC 1 on the coating thickness is negligible. Additionally the coating thickness can be modified by changing the crystallization behavior of sugar and sugar alcohols (polyols) during drying by adding surface-reacted calcium carbonates alone (Formulations 21 and 25) or by adding mixtures of surface-reacted calcium carbonates and calcium carbonates (Formulations 22 and 26).

TABLE 5

Composition of formulations used for coating of chewing gum cores

| Ingredients | % w/w | | | | | | | |
|---|---|---|---|---|---|---|---|---|
| Formula | 19 | 20 | 21 | 22 | 23 | 24 | 25 | 26 |
| $TiO_2$ | 7.5 | — | — | — | 7.5 | — | — | — |
| GCC 1 | — | 525.0 | — | — | — | 525.0 | — | — |
| GCC 2 | — | — | — | 330.0 | — | — | — | 330.0 |
| SRCC 1 | — | — | 120.0 | 75.0 | — | — | 120.0 | 75.0 |
| Crystal sugar | 1492.5 | 975.0 | 1380.0 | 1095.0 | — | — | — | — |
| Malitol | — | — | — | — | 1492.5 | 975.0 | 1380.0 | 1095.0 |
| Aqua dem. | 500.0 | 500.0 | 500.0 | 500.0 | 642.5 | 642.5 | 642.5 | 642.5 |
| | 2000 | 2000 | 2000 | 2000 | 2142.5 | 2142.5 | 2142.5 | 2142.5 |
| Solids (%) | 75 | 75 | 75 | 75 | 70 | 70 | 70 | 70 |
| Percentage of pigment material in formulation based on solids (%) | 0.5 | 35.0 | 8.0 | 5.0 SRCC 1 + 22.0 GCC 2 | 0.5 | 35.0 | 8.0 | 5.0 SRCC 1 + 22.0 GCC 2 |

The coating formulations containing the crystal sugar were prepared with a solids content of 75 wt.-%, based on the total weight of the coating formulation, i.e. 1 part water and 3 parts of a mix of crystal sugar and pigment material(s). The sugar-free coating formulations containing the sugar alcohol malitol were prepared with a solids content of 70 wt.-%, based on the total weight of the coating formulation, i.e. 1 part of water and 2.33 parts of a mix the sugar alcohol malitol and pigment material(s). The coating formulations were prepared at a temperature between 70 and 80° C. under stirring.

The coating formulations were applied on the gum cores by pouring the coating formulation onto the gum core mass followed by drying with hot air. The drying air had a temperature of 55° C. The application of coating formulation followed by a drying cycle was carried out until a desired coating amount of around 20 to 35% w/w was achieved.

Figure 6:
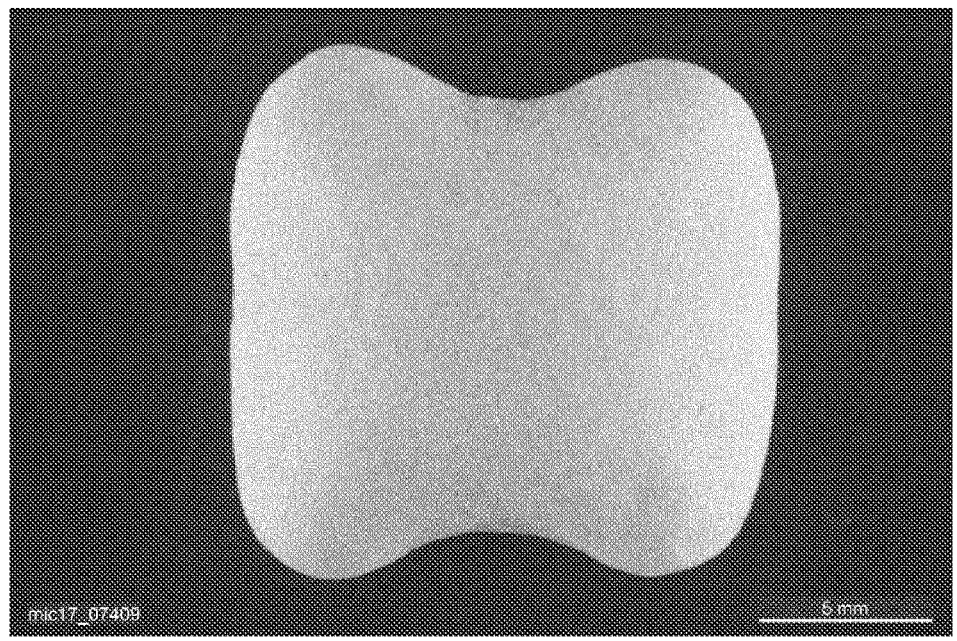
FIG. 6 shows a chewing gum core coated with $TiO_2$
Figure 7:
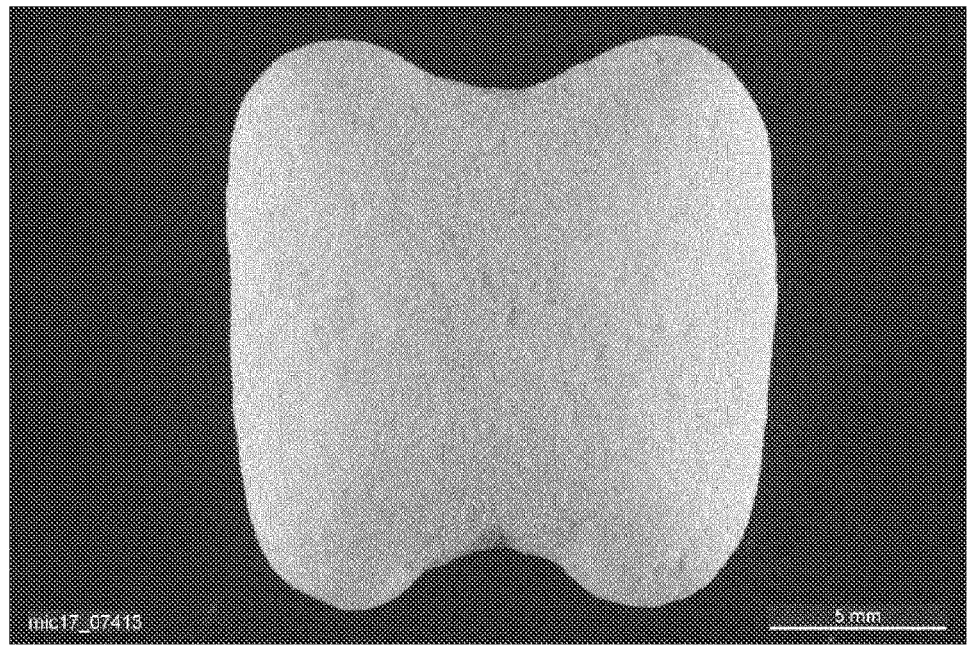
FIG. 7 shows a chewing gum core coated with surface-reacted calcium carbonate

FIGS. 6 & 7 show the chewing gum core coated with formulations 19 (FIGS. 6 and 21 (FIG. 7).

Figure 11:
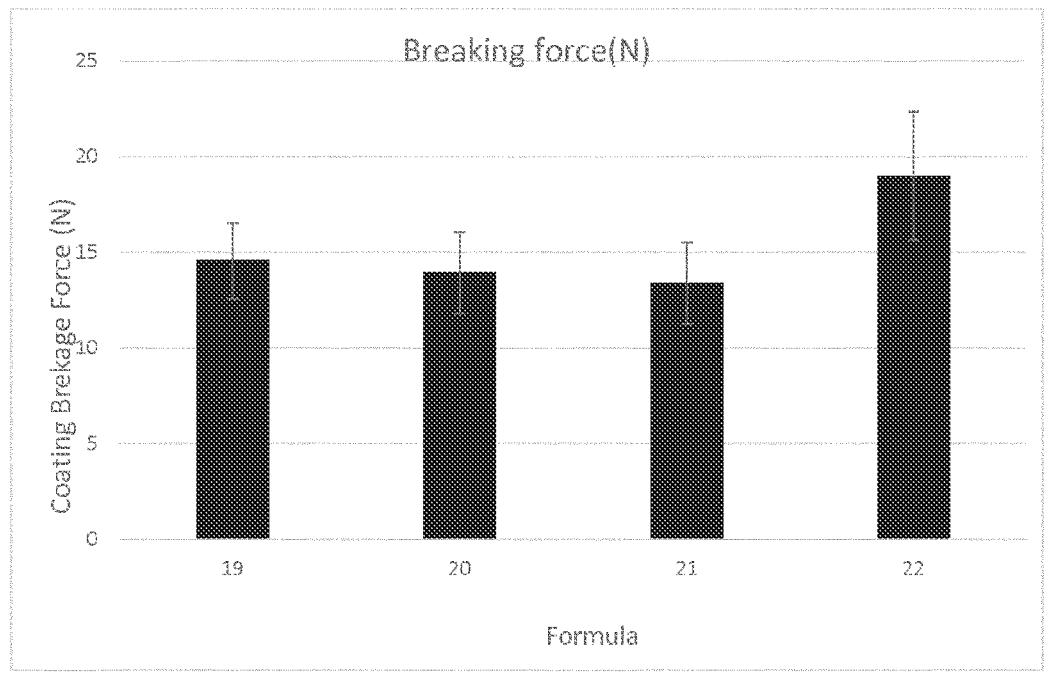
FIG. 11 shows the breakage force of the coatings with various formulations

As can be seen in FIG. 11, there is no significant impact on the coating strength when coating is effected with surface-reacted calcium carbonate (Formulation 21) compared to $TiO_2$ (Formulation 19). This also indicates that there is no negative impact on the physical properties of the coating when coated with surface-reacted calcium carbonate compared to currently market standard $TiO_2$.

C. Measurement of the Drying Time

Method for preparing the coating composition:

All compositions were prepared on the basis of the W/W total solids (TS) in the composition, i.e. 50% TS composition means 50 grams of solids in 100 gram of final composition.

The compositions tested had 27.27% TS; 10% TS and 5% TS.

Despite of changes in TS percentage of composition, the ratio of sugar, water and other components were constant. The SRCC coating composition had 92% sugar and 8% SRCC 1 of solids. The $TiO_2$ composition had 99.5% sugar and 0.5% $TiO_2$ of solids. The reference sugar composition had 100% solids sugars.

Equipment used:

Weighing scale—Mettler Toledo XS603S

Oven for drying the films—Hera Therm oven OMH180-S

Magnetic Stirrer—Variomag Multipoint

Beaker for Mixing—Duran 150 mL

The compositions were prepared in the steps given below:

The required water was weighed in a glass beaker

The sugar was put in water under constant stirring at 600 rpm for 10 min

The SRCC 1 or $TiO_2$ was added in a next step into the sugar composition at constant stirring rate of 600 rpm The composition was mixed under constant stirring of 600 rpm for 20 min The drying of the compositions for film formation was performed in the steps given below:

3 gram of composition were poured on an aluminium plate (Rotilabo Probenschalen 28 mL)

The aluminum plate was gently moved to make a constant film on the plate

The plate was transferred in the oven and dried at 90° C. and the weight of the plate was measured after 30, 60 and 120 minutes (T30, T60 and T120)

The moisture left in the films was calculated by initial weight and weight after drying

TABLE 6

Samples used for the drying experiments

| Sample | Amount of water [g] | Amount of fine powdered sugar [g] | Amount of SRCC 1 or $TiO_2$ [g] |
|---|---|---|---|
| 27% TS-SRCC 1 | 73 | 2.16 | 24.84 |
| 27% TS-$TiO_2$ | 73 | 0.135 | 26.865 |
| 27% TS-Sugar | 73 | 27 | 0 |
| 10% TS-SRCC 1 | 90 | 9.2 | 0.8 |
| 10% TS-$TiO_2$ | 90 | 9.95 | 0.05 |
| 10% TS-Sugar | 90 | 90 | 0 |
| 5% TS-SRCC 1 | 95 | 4.6 | 0.4 |
| 5% TS-$TiO_2$ | 95 | 4.975 | 0.025 |
| 5% TS-Sugar | 95 | 5 | 0 |

TABLE 7

Drying performance at 27% TS

| | Moisture content in film (W/W %) | | | |
|---|---|---|---|---|
| Sample | T0 | T30 | T60 | T120 |
| 27% TS-SRCC 1 | 73.00% | 5.13% | 4.14% | 3.92% |
| 27% TS-$TiO_2$ | 73.00% | 5.75% | 4.65% | 4.33% |
| 27% TS-Sugar | 73.00% | 5.89% | 4.58% | 4.14% |

TABLE 8

Drying performance at 10% TS

| | Moisture content in film (W/W %) | | | |
|---|---|---|---|---|
| Sample | T0 | T30 | T60 | T120 |
| 10% TS-SRCC 1 | 90.00% | 0.95% | 0.51% | 0.51% |
| 10% TS-$TiO_2$ | 90.00% | 1.18% | 0.75% | 0.53% |
| 10% TS-Sugar | 90.00% | 1.30% | 0.87% | 0.87% |

TABLE 9

Drying performance at 5% TS

| | Moisture content in Film (W/W %) | | | |
|---|---|---|---|---|
| Sample | T0 | T30 | T60 | T120 |
| 5% TS-SRCC 1 | 95.00% | 0.14% | 0.03% | 0.03% |
| 5% TS-$TiO_2$ | 95.00% | 0.25% | 0.14% | 0.14% |
| 27% TS-Sugar | 95.00% | 0.75% | 0.54% | 0.32% |

It is clearly demonstrated by the data set out in tables 7 to 9 that a surface-reacted calcium carbonate reduces the moisture content in the prepared films faster than $TiO_2$ and only sugar films and also reduces the drying time. Due to the increased drying performance of the edible composition of the present invention, this composition is suitable as an edible coating and/or filling for a food, pharmaceutical and neutraceutical product.

D. Opacifying Efficiency of Films Prepared from the Edible Compositions

The present example exemplifies the opacifying efficiency of the inventive edible compositions for coatings and/or fillings for food, pharmaceutical and neutraceutical products.

Especially, the opacifying efficiency of surface-reacted calcium carbonate compared to titanium dioxide in films was determined on a weight replacement basis (I g of titanium dioxide replaced by 1 g of surface-reacted calcium carbonate).

A basecoat as described in table 10 below was prepared by using a dispersing mixer (Dispermat) at approx. 1 000 to 2 000 rpm.

TABLE 10 composition of the basecoat

| | parts | g |
|---|---|---|
| PEG 600S (plasticizer) | 4.0 | 20 |
| Water | 85.2 | 426 |
| Pharmacoat 606 (HPMC) | 10.0 | 50 |
| Dimethicone (defoaming agent) | 0.5 | 2.5 |
| SLS (surfactant) | 0.3 | 1.5 |
| Sum | 100.0 | 500 |

This basecoat was used for the preparation of a film with different pigments according to the formulations listed in Table 11 below.

TABLE 11

Films with different pigments

| Film | Basecoat (g) | Pigment | Addition | Ratio HPMC + plasticizer/ pigment |
|---|---|---|---|---|
| 1 | 50 | 13 g $TiO_2$ | 2% Tween 60V Pharma | 7/13 |
| 2 | 50 | 13 g SRCC 1 | 2% Tween 60V Pharma | 7/13 |

The films were prepared as follows:

The Tween 60V Pharma was added into the basecoat under mixing with the dispermat. The pigment was then added to the basecoat. First, the obtained mixture was mixed by hand, then, mixed in a high-speed mixer at 3 000 rpm for 1 min, then mixed by hand again and finally homogenised in a high-speed mixer at 3 000 rpm for 1 min.

Subsequently, films were applied on Leneta contrast cards in accordance with the preparation of a coated surface set out under the measurement methods above. The films were then allowed to dry at ambient temperature until dryness. The characteristics of the films are shown in FIG. 12.

Figure 12:
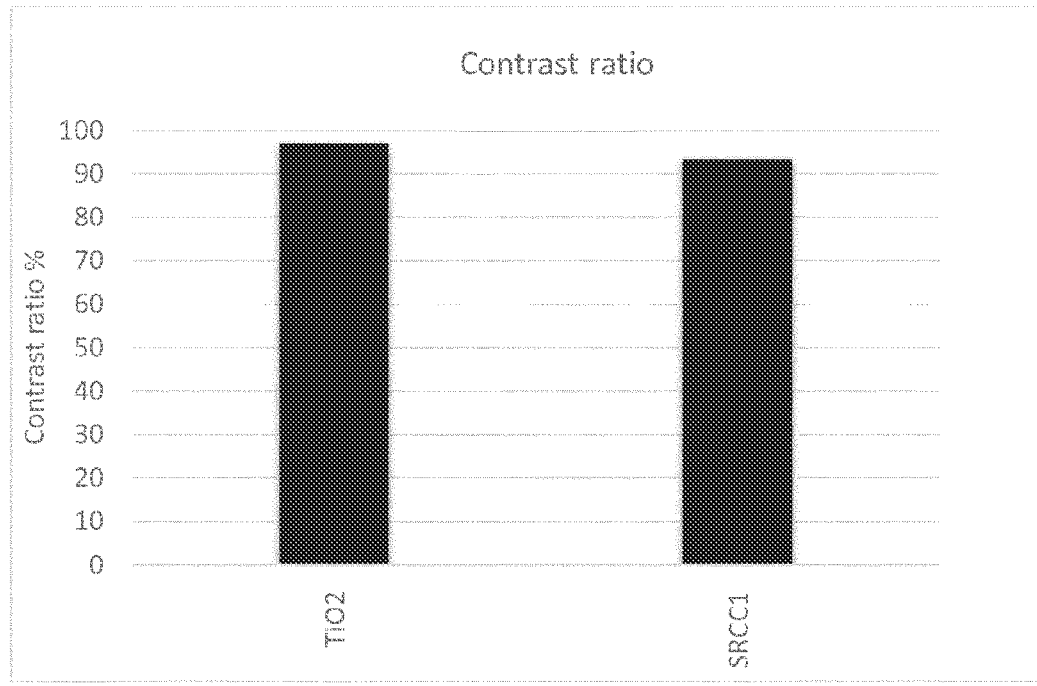
FIG. 12 shows the contrast ratio of non-colour films

From FIG. 12, it can be gathered that a film comprising the surface-reacted calcium carbonate (film 2) shows a similar opacifying efficiency, expressed by the contrast ratio, as a film comprising the same amount of titanium dioxide (film 1).

The basecoat set out in table 10 was also used for the preparation of color films with different pigments according to the formulations listed in Table 12 below as follows:

TABLE 12

Colour films with different pigments

| Film | Basecoat (g) | Pigment | Addition | Ratio HPMC + plasticiser/ pigment/lake |
|---|---|---|---|---|
| SRCC 1 | 50 | 13 g SRCC1 | 2% Tween 60V Pharma | 13/7/4 |
| $TiO_2$ | 50 | 13 g TiO2 | 2% Tween 60V Pharma | 13/7/4 |

The Tween 60V Pharma was added into the basecoat under mixing with the dispermat. The pigment was then added to the basecoat. First, the obtained mixture was mixed by hand, then, mixed in a high-speed mixer at 3 000 rpm for 1 min, then mixed by hand again and finally homogenised in a high-speed mixer at 3 000 rpm for 1 min. Al-carmine lake pigment (Al-Carmine Lake 50%, FCCII, E120) was then added to the mixture and mixed by hand and then in a high-speed mixer for 15 minutes.

Subsequently, films were applied on Leneta contrast cards in accordance with the preparation of a coated surface set out under the measurement methods above. The films were then allowed to div at ambient temperature until dryness. The characteristics of the films are shown in FIG. 12.

Figure 13:
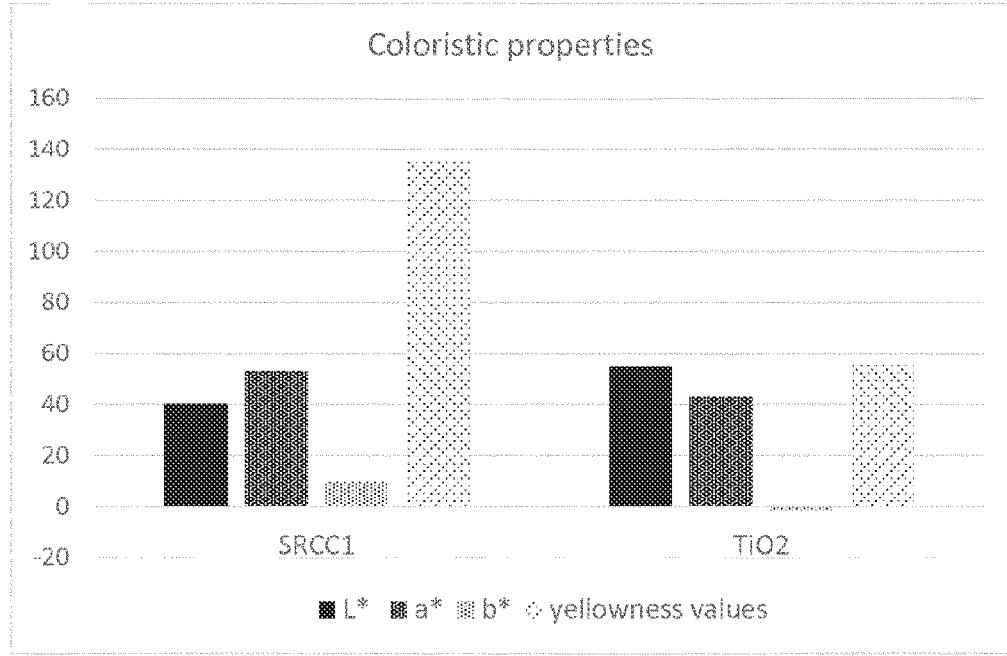
FIG. 13 shows the color characteristics of the films

The color characteristics of the films set out in table 12 were determined. The test was carried out with an Al-Carmine Lake 50%, FCCII, E120 water insoluble powder. The color characteristics of the films are set out in table 13 below and FIG. 13.

TABLE 13

Color characteristics of the films

| Film | L* | a* | b* | Yellowness value |
|---|---|---|---|---|
| $TiO_2$ | 54.77 | 42.86 | −1.64 | 55.42 |
| SRCC 1 | 40.37 | 52.99 | 9.79 | 135.35 |

From the color characteristics of the films, it can be gathered that a film comprising the surface-reacted calcium carbonate has a brighter color than a film comprising the same amount of titanium dioxide.

Summarizing the above, the edible composition of the present invention, i.e. wherein titanium dioxide is replaced by surface-reacted calcium carbonate, is suitable as an edible coating and/or filling for food, pharmaceutical and neutraceutical products, and especially an edible coating for pharmaceutical and neutraceutical products, as it provides a similar opacifying efficiency but a brighter color than a corresponding titanium dioxide containing composition.

The invention claimed is:

1. A method for producing a food product or pharmaceutical product or nutraceutical product at least partially coated and/or filled with an edible composition comprising:
   a) mixing water and/or at least one edible oil with ground calcium carbonate and a surface reacted calcium carbonate having a volume median particle size d50 from 0.1 to 90 μm and a specific surface area of from 15 $m^2$/g to 200 $m^2$/g, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, for obtaining an edible composition, and
   b) applying the edible composition obtained in step a), one or more times, at least partially on the surface of a food product or pharmaceutical product or nutraceutical product, or filling the edible composition obtained in step a) into a food product or pharmaceutical product or nutraceutical product, wherein the edible composition is a food coating, sugar coating, sugar-free coating, nutra coating, food decoration, food filling, pharmaceutical coating, or a combination thereof.

2. The method according to claim 1, wherein applying the edible composition obtained in step a) at least partially on the surface of a food product or pharmaceutical product or nutraceutical product in step b) is carried out by brushing or pouring, pan coating, curtain or dip coating, fluidized bed coating, hot melt coating and/or compression coating or the filling of the edible composition obtained in step a) into a food product or pharmaceutical product or nutraceutical product in step b) is carried out by injecting the edible composition into the food product or pharmaceutical product or nutraceutical product.

3. The method of claim 1, wherein the surface-reacted calcium carbonate has a volume median particle size $d_{50}$ from 0.5 to 50 μm.

4. The method of claim 1, wherein the surface-reacted calcium carbonate has a volume median particle size $d_{50}$ from 1 to 40 μm.

5. The method of claim 1, wherein the surface-reacted calcium carbonate has a volume median particle size $d_{50}$ from 1.2 to 30 μm.

6. The method of claim 1, wherein the surface-reacted calcium carbonate has a volume median particle size $d_{50}$ from 1.5 to 15 μm.

7. The method of claim 1, wherein the surface-reacted calcium carbonate has a specific surface area of from 20 $m^2$/g to 180 $m^2$/g, measured using nitrogen and the BET method.

8. The method of claim 1, wherein the surface-reacted calcium carbonate has a specific surface area of from 25 $m^2$/g to 160 $m^2$/g, measured using nitrogen and the BET method.

9. The method of claim 1, wherein the surface-reacted calcium carbonate has a specific surface area of from 27 $m^2$/g to 150 $m^2$/g, measured using nitrogen and the BET method.

10. The method of claim 1, wherein the surface-reacted calcium carbonate has a specific surface area of from 30 $m^2$/g to 140 $m^2$/g, measured using nitrogen and the BET method.

11. The method of claim 1, wherein the surface-reacted calcium carbonate is a pacifier and/or sweetness reduction agent and/or calorie reduction agent.

12. The method of claim 1, wherein the surface-reacted calcium carbonate has a volume median particle size $d_{50}$ from 0.1 to 75 µm.

13. A method for producing a food product or pharmaceutical product or nutraceutical product at least partially coated comprising:
   a) mixing water and/or at least one edible oil with ground calcium carbonate and a surface reacted calcium carbonate having a volume median particle size $d_{50}$ from 0.1 to 90 µm and a specific surface area of from 15 m$^2$/g to 200 m$^2$/g, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, for obtaining an edible composition, and
   b) applying the edible composition obtained in step a), one or more times, at least partially on the surface of a food product or pharmaceutical product or nutraceutical product, wherein the edible composition is a food coating, sugar coating, sugar-free coating, nutra coating, food decoration, pharmaceutical coating, or a combination thereof.

14. The method according to claim 13, wherein applying the edible composition obtained in step a) at least partially on the surface of a food product or pharmaceutical product or nutraceutical product in step b) is carried out by brushing or pouring, pan coating, curtain or dip coating, fluidized bed coating, hot melt coating and/or compression coating of the food product or pharmaceutical product or nutraceutical product.

15. A method for producing a food product or pharmaceutical product or nutraceutical product at least partially filled comprising:
   a) mixing water and/or at least one edible oil with ground calcium carbonate and a surface reacted calcium carbonate having a volume median particle size $d_{50}$ from 0.1 to 90 µm and a specific surface area of from 15 m$^2$/g to 200 m$^2$/g, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, for obtaining an edible composition, and
   b) filling the edible composition obtained in step a) into a food product or pharmaceutical product or nutraceutical product, wherein the edible composition is food filling.

16. The method according to claim 15, wherein filling of the edible composition obtained in step a) into a food product or pharmaceutical product or nutraceutical product in step b) is carried out by injecting the edible composition into the food product or pharmaceutical product or nutraceutical product.

* * * * *